(12) United States Patent
Buettler et al.

(10) Patent No.: US 8,808,293 B2
(45) Date of Patent: Aug. 19, 2014

(54) TROCHANTERIC FEMORAL NAIL AUGMENTABLE

(75) Inventors: Markus Buettler, Solothurn (CH); Simon Stucki, Solothurn (CH); Stefan Wolf, Solothurn (CH); Martin Felder, Solothurn (CH); Stan Kmiec, West Chester, PA (US); Kyle Henning, West Chester, PA (US); Dana Pappalardo, West Chester, PA (US); This Aebi, Solothurn (CH)

(73) Assignee: DePuy Synthes Products, LLC, Raynham, MA (US)

( * ) Notice: Subject to any disclaimer, the term of this patent is extended or adjusted under 35 U.S.C. 154(b) by 60 days.

(21) Appl. No.: 13/352,860

(22) Filed: Jan. 18, 2012

(65) Prior Publication Data

US 2012/0191092 A1 Jul. 26, 2012

Related U.S. Application Data

(60) Provisional application No. 61/435,036, filed on Jan. 21, 2011, provisional application No. 61/477,857, filed on Apr. 21, 2011.

(51) Int. Cl.
*A61B 17/56* (2006.01)

(52) U.S. Cl.
USPC ............................................. 606/64

(58) Field of Classification Search
USPC .................................... 606/62–68
See application file for complete search history.

(56) References Cited

U.S. PATENT DOCUMENTS

| | | | |
|---|---|---|---|
| 5,122,141 A | 6/1992 | Simpson et al. | |
| 6,053,916 A * | 4/2000 | Moore | 623/16.11 |
| 6,443,954 B1 | 9/2002 | Bramlet et al. | |
| 2002/0143333 A1* | 10/2002 | von Hoffmann et al. | 606/67 |
| 2002/0156473 A1 | 10/2002 | Bramlet et al. | |
| 2005/0010223 A1* | 1/2005 | Gotfried | 606/62 |
| 2006/0149247 A1* | 7/2006 | Frigg et al. | 606/64 |
| 2009/0198237 A1 | 8/2009 | Downey et al. | |
| 2009/0326534 A1* | 12/2009 | Yamazaki et al. | 606/65 |
| 2010/0256688 A1 | 10/2010 | Giersch et al. | |

FOREIGN PATENT DOCUMENTS

| | | |
|---|---|---|
| EP | 0 441 577 | 8/1991 |
| WO | 02/098330 | 12/2002 |

* cited by examiner

*Primary Examiner* — Mary Hoffman
*Assistant Examiner* — Tara Carter

(57) ABSTRACT

A device for bone fixation comprises a bone fixation nail extending from a proximal end to a distal end, the distal end having a helical structure configured to engage a bone, the proximal end having an opening extending thereinto and a first sleeve configured for insertion over a proximal portion of the bone fixation nail and through an intramedullary nail hole, the first sleeve permitting the bone fixation nail to move axially therewithin within a predetermined range of movement along with a locking screw configured to limit movement of the bone fixation nail relative to the first sleeve, the locking screw configured to lockingly engage the opening in the bone fixation nail and having a head and a threaded shaft extending distally therefrom.

20 Claims, 24 Drawing Sheets

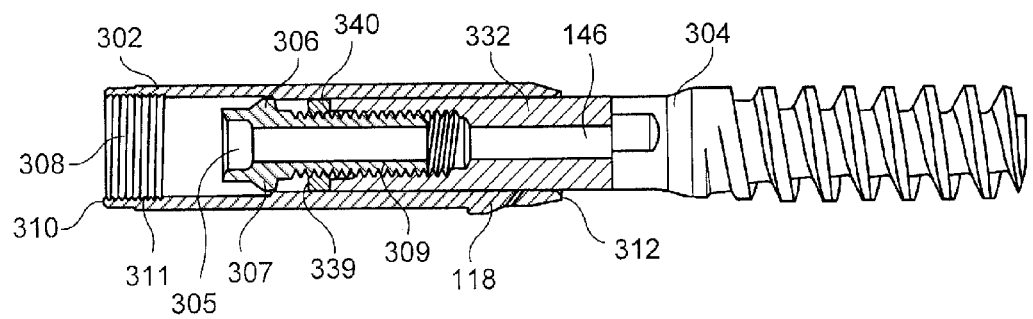
F I G. 10
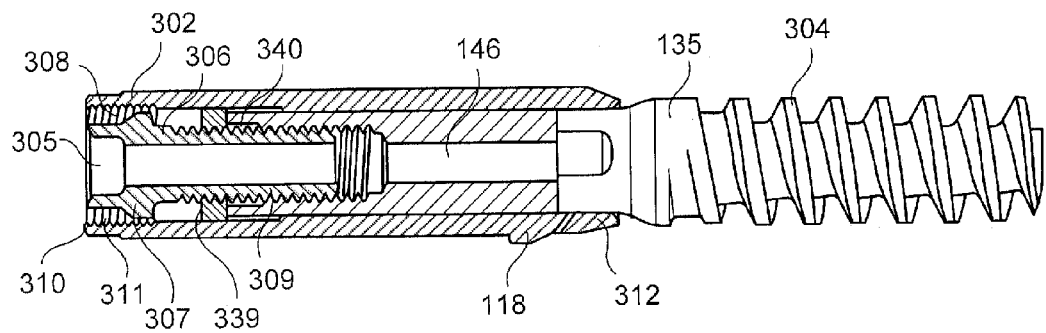
F I G. 11

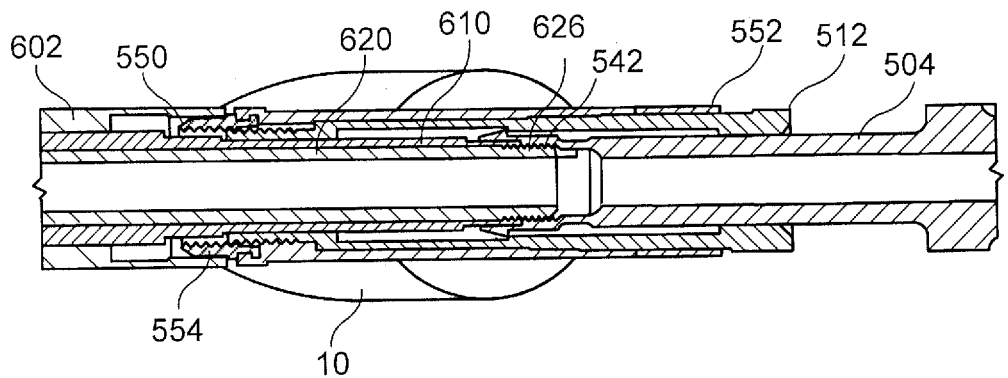
F I G. 26
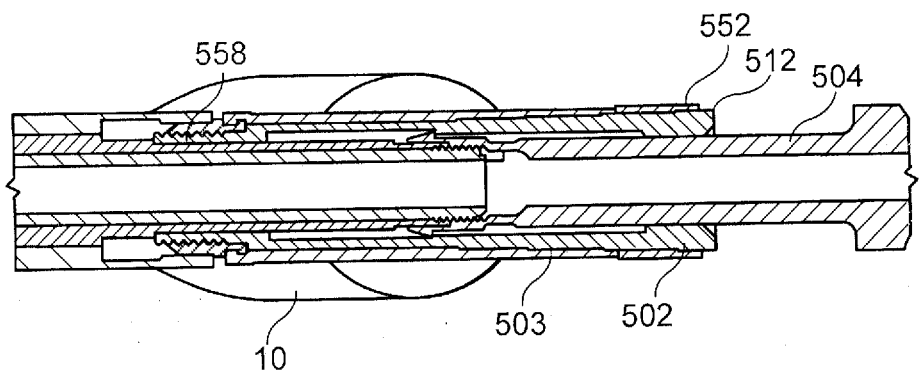
F I G. 27
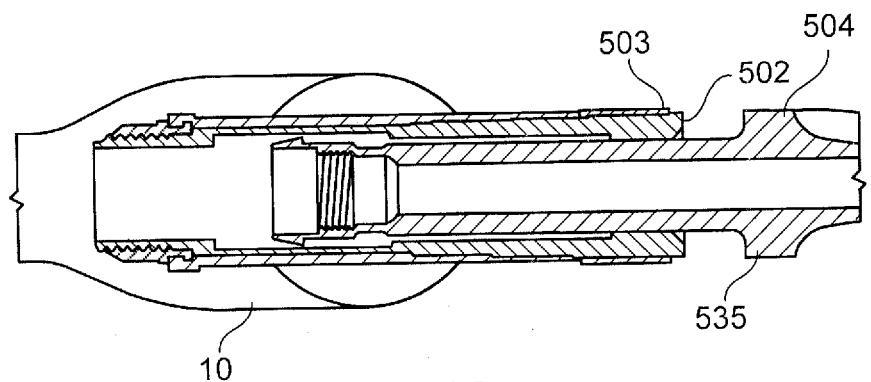
F I G. 28

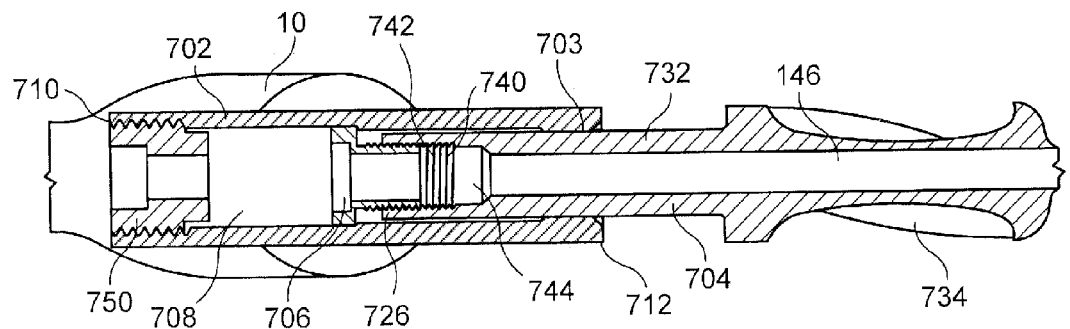
F I G. 30
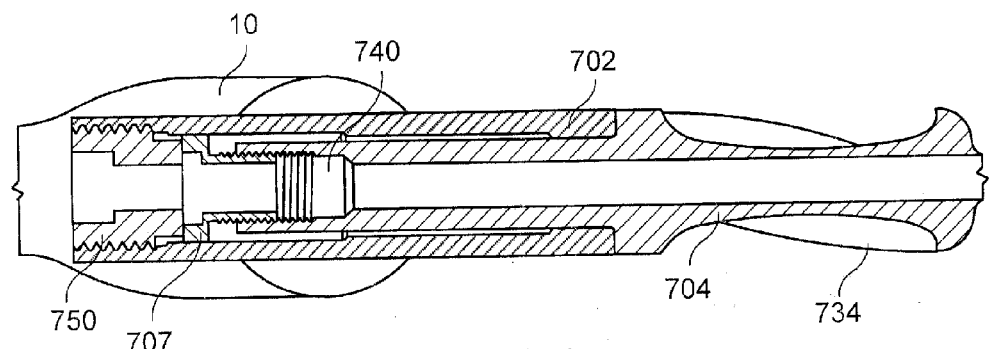
F I G. 31
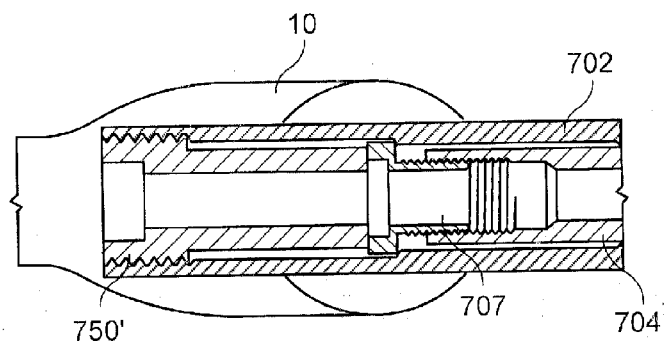
F I G. 32

US 8,808,293 B2

TROCHANTERIC FEMORAL NAIL AUGMENTABLE

PRIORITY CLAIM

The present application claims priority to U.S. Provisional Application Ser. No. 61/435,036 filed on Jan. 21, 2011 and entitled "Trochanteric Femoral Nail Augmentable" and U.S. Provisional Application Ser. No. 61/477,857 filed on Apr. 21, 2011 and entitled "Trochanteric Femoral Nail Augmentable," the entire disclosures of which is incorporated herein by reference.

FIELD OF THE INVENTION

The present invention generally relates to devices and methods for the fixation and stabilization of intertrochanteric fractures. In particular, the present invention relates to a telescoping multi-component bone fixation system having an outer sleeve configured to receive a bone fixation nail therethrough, the bone fixation nail being configured for locking engagement with the bone. One or more locking screws and/or endcaps are provided to lock a position of the bone fixation nail once the nail has been positioned as desired relative to the outer sleeve.

BACKGROUND

Fractures are often treated with screws or other fixation devices inserted into or through a bone to stabilize fractured portions thereof once they have been brought into corrective alignment. Trochanteric bone fixation treatments comprise the insertion of an intramedullary nail into a medullary cavity of a bone and a subsequent insertion of a bone fixation nail into a condylar portion of the bone at an angle relative to the intramedullary nail (i.e., along an axis of the trochanter). Once implanted conventional trochanteric bone fixation devices permit medial and lateral migration of the bone fixation nail within and sometimes out of an outer periphery of the bone. Furthermore, conventional bone fixation devices comprise multiple elements that add to the complexity of bone fixation procedures while minimizing the degree of adjustability of the components relative to one another. Accordingly, this prevents the tailoring of these bone fixation devices to individual requirements of various patients. Such systems therefore reduce the anchoring strength of the bone fixation devices increasing the likelihood of further fractures or other complications.

SUMMARY OF THE INVENTION

The present invention is directed to a device for bone fixation, comprising a bone fixation nail extending from a proximal end to a distal end, the distal end having a helical structure configured to engage a bone, the proximal end having an opening extending thereinto and a first sleeve configured for insertion over a proximal portion of the bone fixation nail and through an intramedullary nail hole, the first sleeve permitting the bone fixation nail to move axially therewithin within a predetermined range of movement along with a locking screw configured to limit movement of the bone fixation nail relative to the first sleeve, the locking screw configured to lockingly engage the opening in the bone fixation nail and having a head and a threaded shaft extending distally therefrom.

BRIEF DESCRIPTION OF THE DRAWINGS

FIG. 10 shows a first partial cross-sectional view of the system of FIG. 9;

FIG. 11 shows a second partial cross-sectional view of the system of FIG. 9;

FIG. 26 shows a first partial cross-sectional view of the tool of FIG. 25 with the system of FIG. 19;

FIG. 27 shows a second partial cross-sectional view of the tool of FIG. 25 with the system of FIG. 19;

FIG. 28 shows a third partial cross-sectional view of the tool of FIG. 25 with the system of FIG. 19;

FIG. 30 shows a first partial cross-sectional view of the system of FIG. 29;

FIG. 31 shows a second partial cross-sectional view of the system of FIG. 29;

FIG. 32 shows a third partial cross-sectional view of the system of FIG. 29;

DETAILED DESCRIPTION

Figure 1:
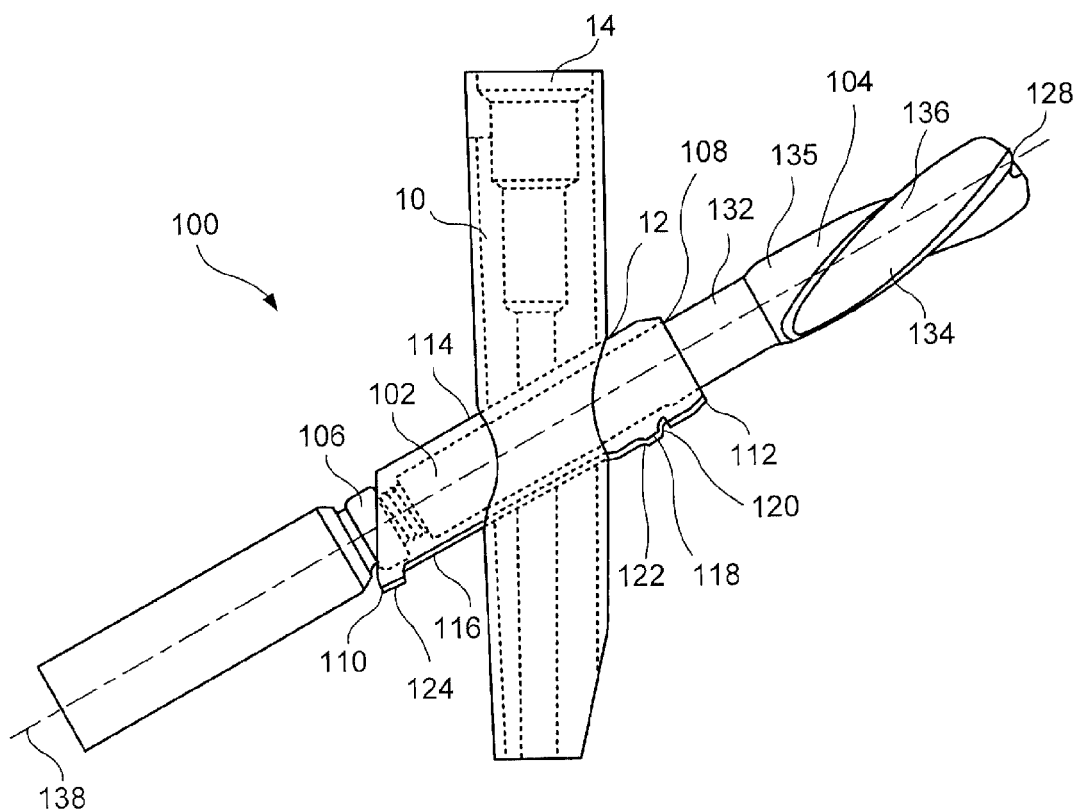
FIG. 1 shows a perspective view of a bone fixation system according to a first exemplary embodiment of the present invention.

The present invention may be further understood with reference to the following description and the appended drawings. The present invention relates generally to devices and methods for the fixation and stabilization of intertrochanteric fractures. It is noted that although embodiments of the present invention have been described with respect to particular bones, the present invention may also be employed in any other bone fixation procedures including, but not limited to, the fixation of femoral fractures and fractures of other long bones. The present invention relates to a telescoping multi-component bone fixation system having an outer sleeve configured to receive a bone fixation nail therethrough, the bone fixation nail being configured for locking engagement with the bone. One or more locking screws and/or endcaps are provided to lock a position of the bone fixation nail once the nail has been positioned as desired relative to the outer sleeve. Specifically, an exemplary outer sleeve according to the invention comprises a locking element configured to lockingly engage an intramedullary nail through which it is inserted to limit a lateral migration thereof within a desired range when implanted in the bone. The exemplary bone fixation nail according to the invention is configured for rotatable insertion through the outer sleeve and into the bone. The bone fixation nail and outer sleeve of the invention are configured so that a lateral and medial movement thereof after implantation remains within a predetermined desired range. The term proximal, as used herein, refers to a direction approaching a physician or other user while the term distal refers to a direction approaching a target portion of a fractured or otherwise damaged bone.

As shown in FIGS. 1-4, a bone fixation system 100 according to the invention comprises an outer sleeve 102, a bone fixation element 104 configured for insertion through the outer sleeve 102 and a locking screw 106 configured for insertion into the bone fixation element 104. The outer sleeve 102 comprises a longitudinal channel 108 extending therethrough along a longitudinal axis 138 from a proximal end 110 to a distal end 112 and may be shaped as, for example, an elliptical (e.g., oblong) cylinder to prevent rotation of the outer sleeve 102 relative to an intramedullary nail 10 through which the outer sleeve 102 may be inserted. It will be understood by those of skill in the art, however, that the outer sleeve 102 may be any of a variety of shapes so long as the outer sleeve 102 is prevented from rotating relative to the intramedullary nail 10. The outer sleeve 102 may be configured so that a first longitudinal side wall 114 has a first length and a second longitudinal side wall 116 has a second length greater than the first length such that the proximal end 110 is substantially oblique. This reduces possible harm to the patient's soft tissue and prevents the proximal end 110 of the outer sleeve 102 from extending too far from a lateral cortex of a bone through which it is inserted. In an exemplary embodiment, a difference in length between the opposing first and second side walls 114, 116 may be approximately equivalent to a length of a head 107 of the locking screw 106 so that the locking screw 106 may be seated at least partially within the outer sleeve 102 in an operative configuration to reduce a degree of external stresses applied thereto after implantation. The second side wall 116 further comprises a first barb 118 located adjacent the distal end 112 of the outer sleeve 102. The first barb 118 protrudes from the outer sleeve 102 by a length sufficient to permit engagement thereof with a peripheral wall of an intramedullary nail hole 12, as will be described in greater detail hereinafter. A distal face of the first barb 118 has an angled wall 120 tapering toward a distal direction so that a radially compressive force applied to the angled wall 120 (e.g. during distal advancement into an intramedullary nail 10) compresses the first barb 118 radially inward until it lies substantially flush with the outer wall of the outer sleeve 102. A proximal face of the first barb 118 comprises a proximal wall 122 extending substantially perpendicularly from the outer sleeve 102. Accordingly, once the first barb 118 has been advanced through the intramedullary nail 10, the barb 118 springs radially outward under its natural bias to engage the proximal wall 122 with the peripheral wall of the intramedullary nail hole 12 thereby preventing proximal retraction of the outer sleeve 102 from the intramedullary nail 10. Thus, the bone fixation element 104 is also prevented from migrating proximally once inserted through the sleeve 102, thereby preventing a loss of fixation. The outer sleeve 102 further comprises a second barb 124 adjacent the proximal end 110 of the outer sleeve 102 and aligned with the second side wall 116. The second barb 124 extends from the outer sleeve 102 substantially perpendicular thereto and is configured to limit a depth of insertion of the outer sleeve 102 into the intramedullary nail hole 12.

Figure 2:
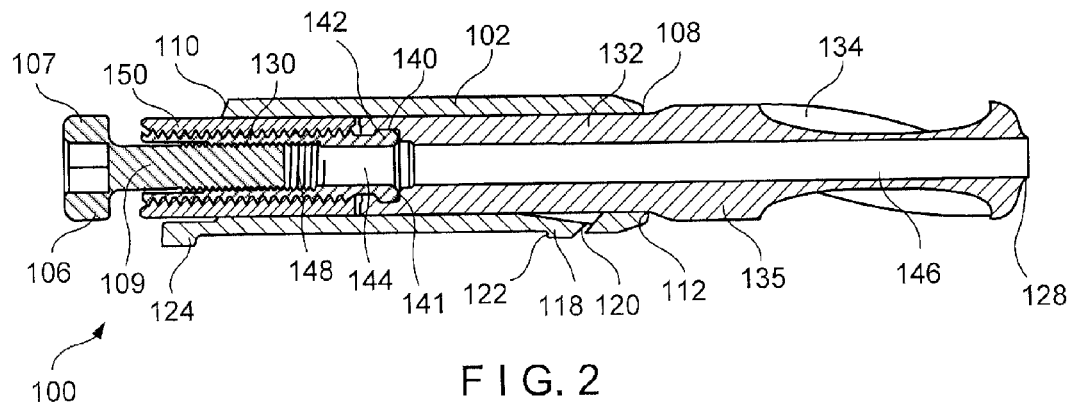
FIG. 2 shows a first partial cross-sectional view of the device of FIG. 1.
Figure 3:
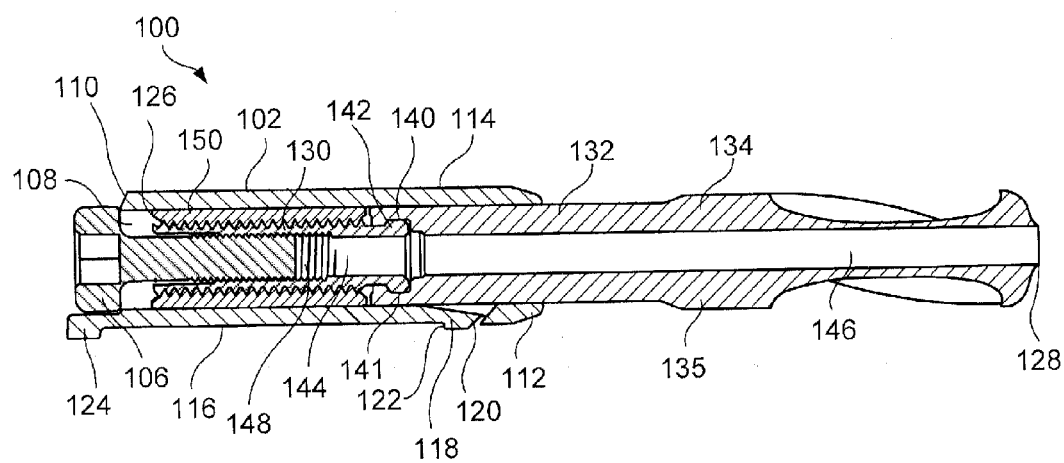
FIG. 3 shows a second partial cross-sectional view of the device of FIG. 1.

The bone fixation system 100 further comprises the bone fixation element 104 configured and dimensioned for insertion through the channel 108 of the outer sleeve 102. The bone fixation element 104 extends from a proximal end 126 to a distal end 128 and comprises a proximal threaded portion 130, a middle substantially cylindrical portion 132 and a distal blade 134 (in this exemplary embodiment the blade 134 is helical). A proximal portion of the blade 134 has an increased outer diameter 135 greater than an inner diameter of the outer sleeve 102 to prevent proximal retraction of the blade 134 into the outer sleeve 102 beyond the extent defined by contact between the proximal end of the blade 134 and the outer sleeve 102. It is further noted that although the blade 134 of FIGS. 1-3 is depicted with notches 136 extending helically along the bone fixation element 104, any other type of blades and/or threading may be used without deviating from the scope of the invention. For example, the blade 134 may comprise threads or notches that extend substantially helically over the distal portion of the element 104 at any angle relative to the longitudinal axis 138, as shown, for example, in FIGS. 9-15.

The proximal threaded portion 130 has a first diameter smaller than a second diameter of the cylindrical portion 132 and is configured to be at least partially inserted into an opening 140 extending into the cylindrical portion 132. Specifically, a distal end of the threaded portion 130 comprises a lip 142 configured and dimensioned to lockingly engage a groove 141 in the opening 140 of the cylindrical portion 132. The threaded portion 130 may be rotatable relative to the cylindrical portion 132. In an exemplary embodiment, the proximal threaded portion 130 may be fitted within the opening 140 during manufacturing so that a central longitudinal channel 144 extending through the proximal threaded portion 130 is open to and aligned with a central longitudinal channel 146 extending through the cylindrical portion 132 and the blade 134. In an exemplary embodiment, the channels 144, 146 are open at the proximal and distal ends 126, 128 to permit insertion of a medical tool or injectable material (e.g., a bone strengthening material) therethrough. Alternatively, the channels 144, 146 may receive a guide wire therethrough such that the bone fixation element 104 may be slid over the guide wire and into the bone. A predetermined length of a proximal portion of the channel 144 may be provided with threading 148 configured to permit threaded engagement with the locking screw 106, as will be described in greater detail below. The threading 148 may also permit compression of a fracture of the bone and/or removal of the bone fixation element 104.

Figure 4:
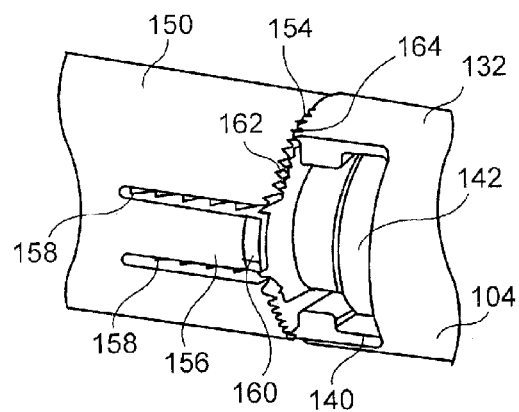
FIG. 4 shows a zoomed partial cross-sectional view of the device of FIG. 1.
Figure 5:
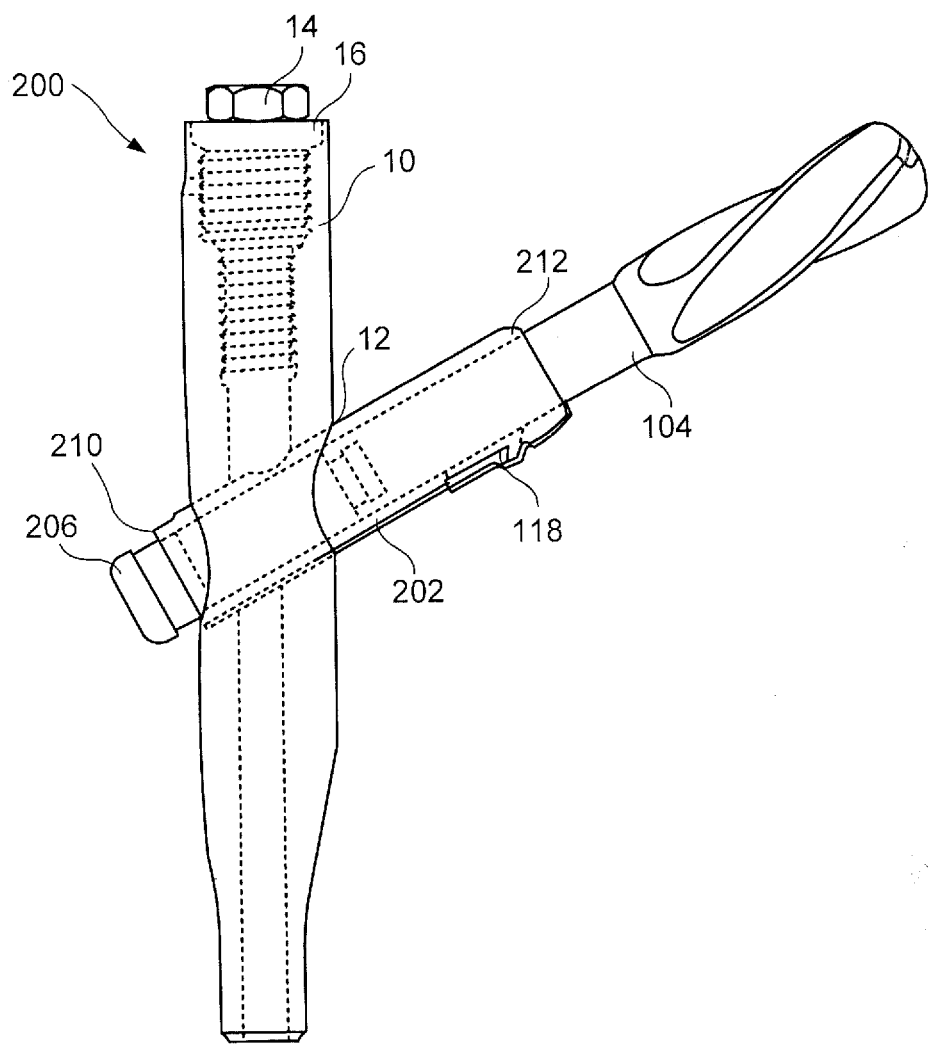
FIG. 5 shows a perspective view of a bone fixation system according to a second exemplary embodiment of the present invention.
Figure 6:
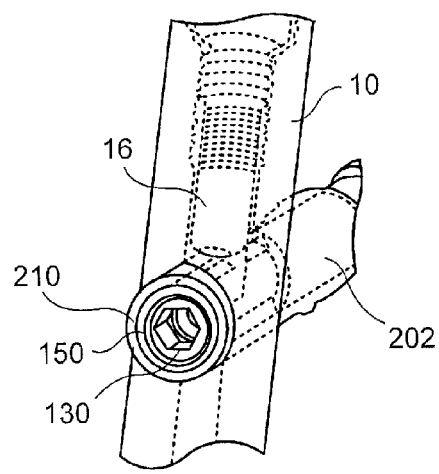
FIG. 6 shows a first perspective view of the system of FIG. 5.

The proximal threaded portion 130 is configured to threadedly receive a connector 150 thereover. The connector 150 has an outer diameter substantially equivalent to an outer diameter of the cylindrical portion 132 and an inner diameter of the outer sleeve 102. In an exemplary embodiment, the connector 150 is threadedly attached to the bone fixation element 104 prior to insertion thereof through the outer sleeve 102. The connector 150 is substantially cylindrical and extends from a proximal end 152 to a distal end 154. For example, the connector 150 may include a flat surface extending along a length thereof and corresponding to a flat surface of the channel 108. As shown in FIG. 4, a distal portion of the connector 150 comprises at least one tab 156 defined by first and second slots 158 extending proximally from the distal end 154. A distal end of the tab 156 comprises a notch 160 extending radially outward from the connector 150 by a predetermined distance. The notch 160 may engage a portion of an insertion instrument to prevent the system 100 from being disassembled therefrom. It is noted that although the present embodiment has been described with one tab 156, any number of tabs 156 may be provided over the connector 150 in any arrangement without deviating from the scope of the invention. The distal end 154 of the connector 150 may also be provided with a serrated, notched, or otherwise treated surface 162 configured and dimensioned to engage a respectively formed surface 164 on a proximal end of the cylindrical portion 132. As those skilled in the art will understand, engagement of the treated surfaces 162, 164 prevents rotation of the connector 150 relative to the cylindrical portion 132 which, in turn, prevents rotation of the proximal threaded portion 130 relative to the cylindrical portion 132. The connector 150 may also be keyed to an inner surface of the channel 108 of the outer sleeve 102 such that when combined with the engagement of the treated surfaces 162, 164, the bone fixation element 104 is prevented from rotating relative to the opening 12 of the intramedullary nail 10.

The exemplary locking screw 106 of the invention has a head 107 having an outer diameter greater than an inner diameter of the outer sleeve 102 and a threaded shaft portion 109 extending distally therefrom, wherein one of a predetermined portion and an entire length of the shaft 109 is threaded. The locking screw 106 is configured to control a depth of lateral movement of bone fixation element 104 within the bone after implantation. Specifically, a depth of insertion of the locking screw 106 within the proximal threaded portion 130, along with an axially slidable movement of the bone fixation screw 106 within the outer sleeve 102 permits a physician or other user to control a range of movement of the bone fixation element 104 within the bone. One such embodiment is depicted in FIGS. 2 and 3, wherein the locking screw 106 is inserted to a first target depth to permit a lateral movement of the bone fixation element 104 within the outer sleeve 102 by ±10 mm. Specifically, in FIG. 2, the shaft 109 is screwed into the proximal threaded portion 130 by a first depth selected so that when the head 107 contacts the proximal end 110 of the outer sleeve 102, the increased diameter portion 135 is separated from the distal end 112 of the outer sleeve 102 by approximately 10 mm. It is noted however that this range may be increased or decreased as desired by the surgeon by changing a depth of insertion of the shaft 109 within the proximal threaded portion 130. FIG. 3 depicts the system of FIG. 2 when the fixation element 104 has been retracted proximally within the outer sleeve 102 (e.g., under normal force exertion during/after implantation). Proximal movement of the bone fixation element 104 within the outer sleeve 102 is limited by engagement of the increased diameter portion 135 with the distal end 112 of the outer sleeve 102.

In accordance with an exemplary method for the bone fixation system 100, a fractured or otherwise damaged bone (not shown) is brought into corrective alignment and the intramedullary nail 10 is inserted into a medullary cavity thereof to a target position and orientation therein in any known manner. The bone fixation element 104 is then inserted through the intramedullary nail hole 12 to a target depth until the increased diameter portion 135 has moved distally out of the intramedullary nail 12. The outer sleeve 102, the bone fixation element 104 and the connector 150 may be pre-assembled and inserted through the intramedullary nail hole 12 to a target depth until the first barb 118 has at least passed through the nail hole 12. Once the outer sleeve 102, the bone fixation element 104 and the connector 106 are positioned within the hole 12, as desired, the locking screw 106 may be inserted therein. As described in greater detail earlier, during insertion through the nail hole 12, engagement of the angled wall 120 with an inner wall of the intramedullary nail hole 12 causes the first barb 118 to be radially compressed until it lies substantially flush against the outer sleeve 102 as it moves distally out of the intramedullary nail hole 12. Once the radially compressive force is removed (i.e., when the first barb 118 moves distally out of the nail hole 12), the first barb 118 returns to a biased configuration extending radially outward from the outer sleeve 102 by a predetermined distance. In this configuration, the first barb 118 is prevented from being retracted proximally out of the intramedullary nail hole 12 due to engagement of the proximal wall 122 with the outer periphery of the intramedullary nail hole 12. Once the bone fixation system 100 is properly seated within the bone, an intramedullary nail locking screw (not shown) is inserted into a locking screw hole 14 of the intramedullary nail 10 until a distal end thereof contacts the outer sleeve 102 to apply a compressive retaining force thereto, as those skilled in the art will understand.

Figure 7:
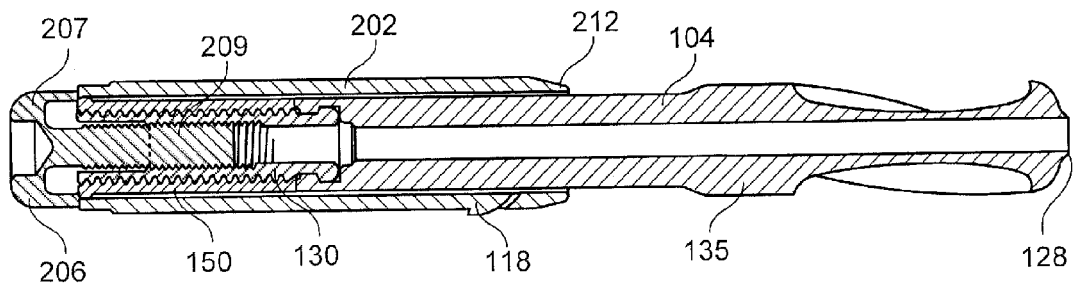
FIG. 7 shows a first partial cross-sectional view of the device of FIG. 5.
Figure 8:
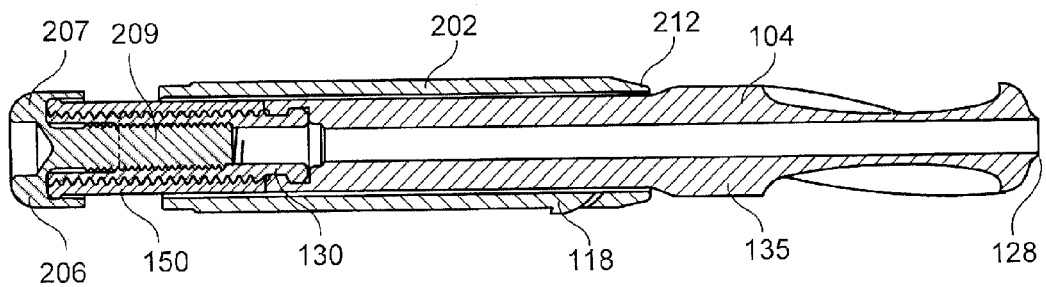
FIG. 8 shows a second partial cross-sectional view of the device of FIG. 5.
Figure 9:
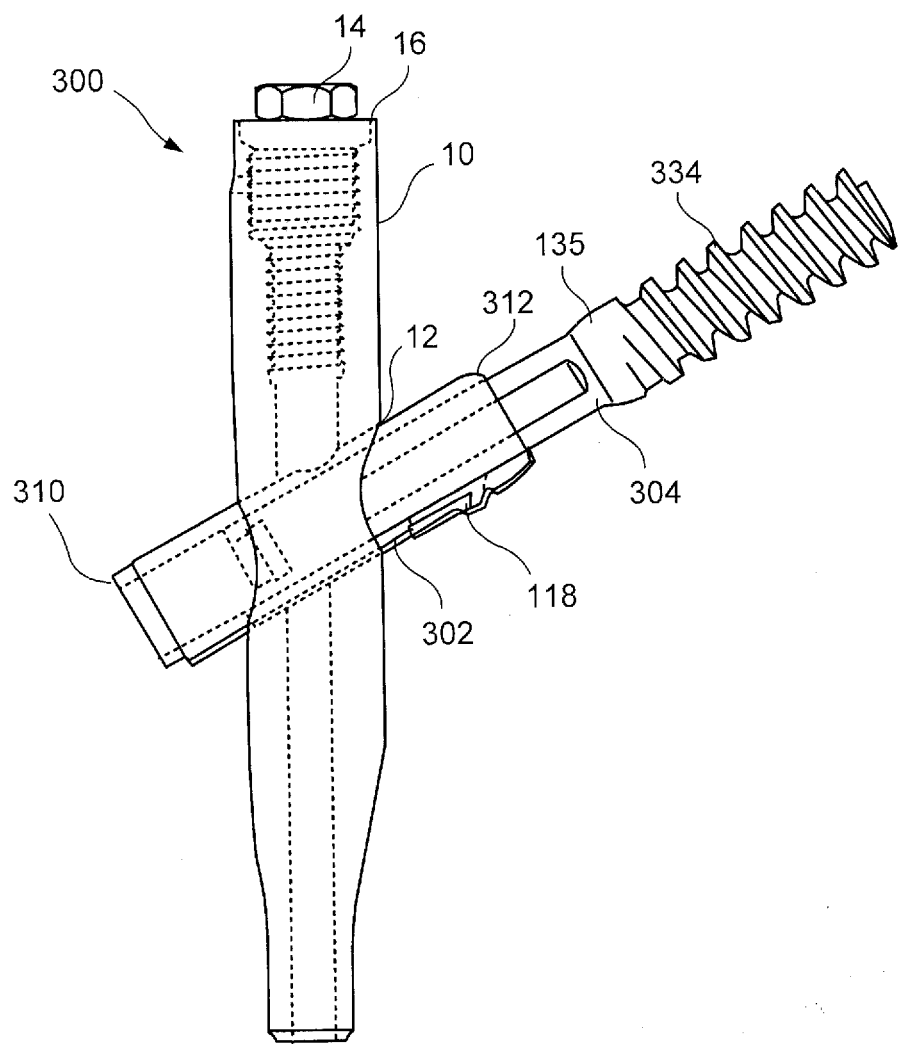
FIG. 9 shows a perspective view of a bone fixation system according to a third exemplary embodiment of the present invention.

FIGS. 5-8 depict a bone fixation system 200 according to a another embodiment of the invention. The bone fixation system 200 is formed substantially similarly to the bone fixation system 100 of FIG. 1, wherein like elements have been referred to with like reference numerals. Specifically, the system 200 comprises an outer sleeve 202 formed substantially similarly to the outer sleeve 102 and extending from a proximal end 210 to a distal end 212. Similarly to the outer sleeve 102, the outer sleeve 202 may be an elliptical cylinder. However, unlike the outer sleeve 102, the outer sleeve 202 has a uniform longitudinal length. The bone fixation system 200 further comprises the protection cap 206 in lieu of the locking screw 106. The protection cap 206 allows for a compression, as shown in FIG. 7, and comprises a head 207 having an outer diameter greater than an inner diameter of the outer sleeve 202 and a threaded shaft 209 extending distally from the head 207. The bone fixation system 200 operates in substantially the same manner as the bone fixation system 100 of FIGS. 1-4, with the bone fixation element 104 being axially movable relative to the outer sleeve 202 by approximately ±10 mm. The bone fixation element 104 of FIGS. 5-8 is prevented from moving distally relative to the outer sleeve 202 beyond a limit set by engagement of the head 207 with the proximal end 210 of the outer sleeve 202 and is prevented from moving proximally relative to the outer sleeve 202 due to engagement of the increased diameter portion 135 with the distal end 212 of the outer sleeve 202.

As shown in FIGS. 9-15, a bone fixation system 300 according to a further embodiment of the invention is substantially similar to the bone fixation system 100 of FIGS. 1-4, wherein like elements have been referenced with like reference numerals. The bone fixation device 100 comprises an outer sleeve 302 extending from a proximal end 310 to a distal end 312 and having a channel 308 extending longitudinally therethrough. A predetermined length of a proximal portion of the outer sleeve 302 is provided with internal threading 311 for engaging an insertion tool which inserts the outer sleeve 302 through the nail 10 over the head element 304. The outer sleeve 302 is configured and dimensioned to receive a bone fixation element 304 therethrough, the bone fixation element 304 having a threaded portion 334, cylindrical body portion 332 and an opening 340 extending into a proximal end of the cylindrical body portion 322. However, whereas the opening 140 of the bone fixation system 100 is configured to lockingly engage the proximal threaded portion 130, the exemplary opening 340 of FIGS. 9-15 extends distally into a proximal end 339 of the cylindrical body 322 by a depth sufficient to permit threaded engagement directly with a locking screw 306. The opening 340 may be open to the central longitudinal channel 146 extending through the cylindrical portion 332 and threaded portion 304, as described in greater detail earlier.

The exemplary locking screw 306 comprises an elongated threaded shaft portion 309 and a head 307. The shaft portion 309 is configured and dimensioned to threadedly engage threads of the opening 340. An outer diameter of the head 307 is configured to permit insertion thereof into the opening 304 while still permitting complete insertion of the locking screw 306 into the channel 308 of the outer sleeve 302. In an exemplary embodiment, the locking screw 306 further comprises a central longitudinal channel 305 extending therethrough from the head 307 to a distal end of the shaft 309. The channel 305 has substantially the same diameter as the central longitudinal channel 146 extending through the cylindrical portion 332 and threaded portion 304. Accordingly, when the locking screw 306 is inserted into the cylindrical portion 332, the central longitudinal channel 305 is longitudinally aligned with and open to the central longitudinal channel 146. The locking screw 306 allows for compression and prevents medial migration of the bone fixation element 304 through the femoral head.

Figure 12:
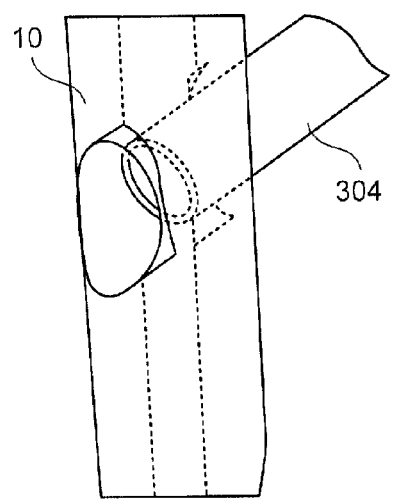
FIG. 12 shows a perspective view of the system of FIG. 9 in a first insertion configuration.
Figure 13:
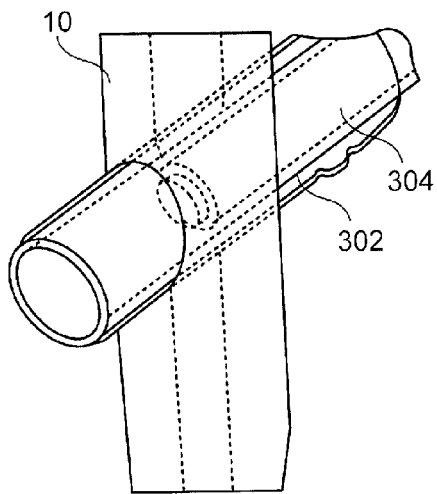
FIG. 13 shows a perspective view of the system of FIG. 9 in a second insertion configuration.
Figure 14:
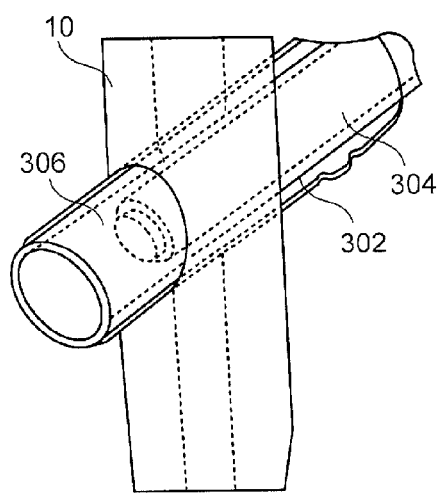
FIG. 14 shows a perspective view of the system of FIG. 9 in a third insertion configuration.
Figure 15:
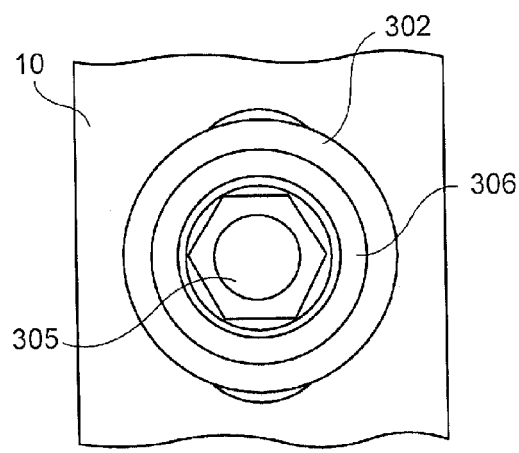
FIG. 15 shows a perspective view of the system of FIG. 9 in a fourth insertion configuration.

As shown in FIG. 12, in a first exemplary step according to the invention, the bone fixation element 304 is inserted over a guide wire into a bone and through a lateral cross-bore of the intramedullary nail 10 until it has reached a target depth within the bone (not shown). The bone fixation element 304 is dimensioned so that when positioned at the target depth, at least a portion of the cylindrical body portion 332 is received within the intramedullary nail 10. As shown in FIG. 13, the outer sleeve 302 is then inserted into the bone and through the cross-bore of the intramedullary nail 10 at least until the first barb 118 is moved out of the cross-bore, as described in greater detail in earlier embodiments. As shown in FIG. 14, the locking screw 306 is then inserted into the opening 340 to a target depth therewithin. The locking screw 306 is configured to limit a range of lateral movement, of the bone fixation element 304 relative to the outer sleeve 302 after insertion into the bone. In addition, the locking screw 306 allows for compression and prevents medial migration of the bone fixation element 304 through the femoral head. As shown in FIG. 15, a longitudinal alignment of the channel 305 with the central longitudinal channel 146 permits an insertion of instruments through the bone fixation system 300 after implantation thereof into the bone.

Figure 16:
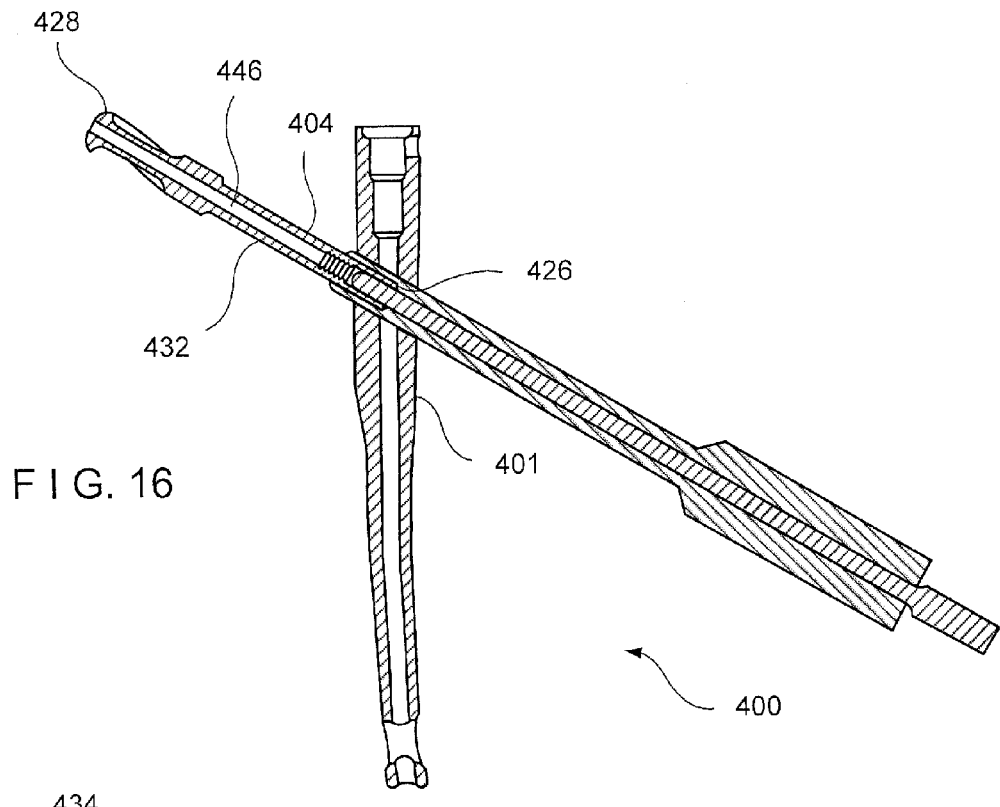
FIG. 16 shows a first partial cross-sectional view of a bone fixation system according to a fourth exemplary embodiment of the present invention.
Figure 17:
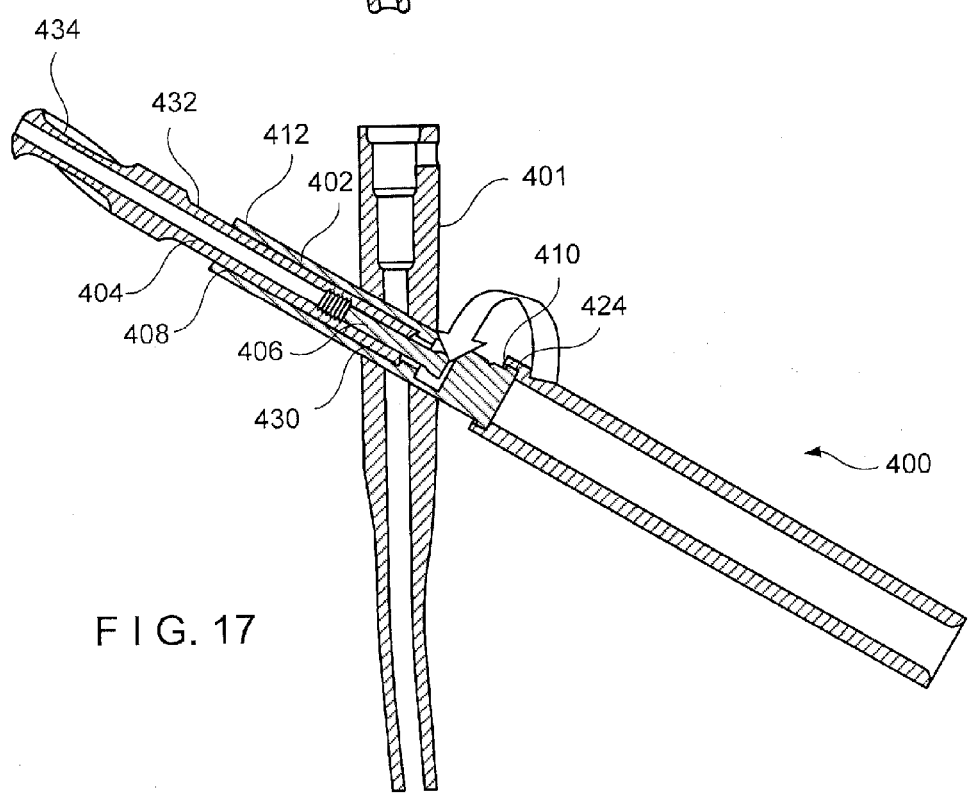
FIG. 17 shows a second partial cross-sectional view of the bone fixation system of FIG. 16.
Figure 18:
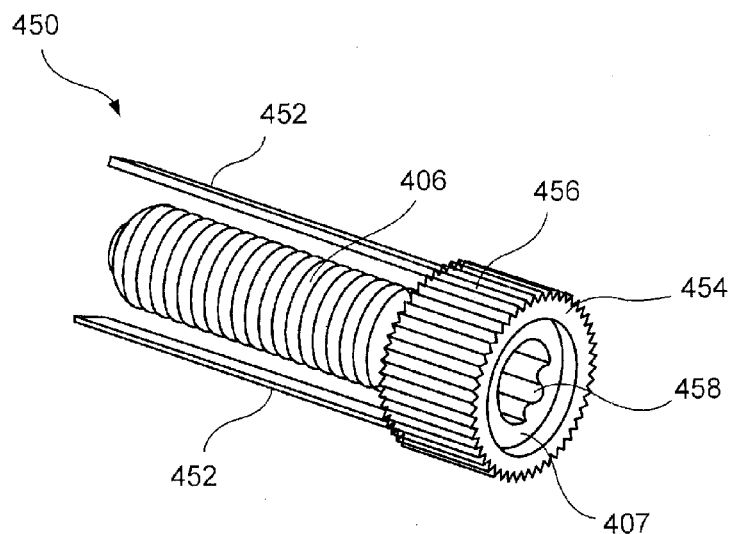
FIG. 18 shows a perspective view of a blocking device for use with the bone fixation system of FIG. 16.

FIGS. 16-18 depict a bone fixation device insertion system 400 according to another embodiment of the invention. Specifically, as shown in FIGS. 16-18, the bone fixation system 400 is substantially similar to the bone fixation system 100 of FIGS. 1-4, with like elements referenced with like reference numerals. The bone fixation device 400 comprises an outer sleeve 402 extending from a proximal end 410 to a distal end 412 and having a channel 408 extending longitudinally therethrough which is received over an inner sleeve 404 extending from a proximal end 426 to a distal end 428 which may include any desired bone engaging structure 434 (e.g., a thread, helical blade, etc.). The outer sleeve 402 also includes a nail engaging structure such as a hemispherical projection 424 which engages a correspondingly shaped recess in the nail to lock the outer sleeve 402 in a desired position and rotational orientation with respect to the nail 401. For example, the nail may include a bayonet groove (not shown) configured to lockingly engage the hemispherical projection 420 after the outer sleeve 402 has been rotated a desired amount (e.g., 180°) therein. An inner surface at the proximal end 410 of the outer sleeve 402 includes a structure 411 (e.g., circular toothwork), which may be engaged by an insertion tool so that the outer sleeve 402 may be rotatably driven distally through the nail into the bone over the inner sleeve 404. The inner sleeve 404 includes a proximal portion 430, a middle cylindrical body portion 432, the bone engaging structure 434 at the distal end 428 with a channel 446 extending therethrough. The proximal portion 430 of the inner sleeve 404 has an outer surface including plurality of flat longitudinally extending surfaces. For example, the proximal portion 430 may be hexagonal. It will be understood by those of skill in the art, however, that the proximal portion 430 may have any of a variety of shapes so long as the outer surface includes at least two flat surfaces, preferably opposing one another.

Figure 19:
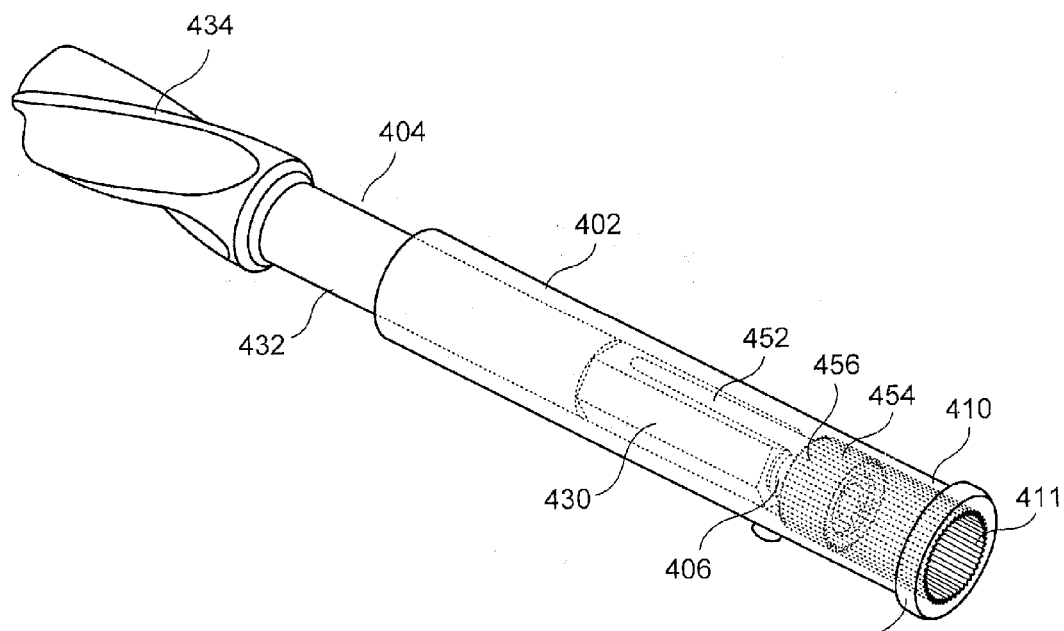
FIG. 19 shows a perspective view of an assembled inner and outer sleeve according to the bone fixation system of FIG. 16.
Figure 20:
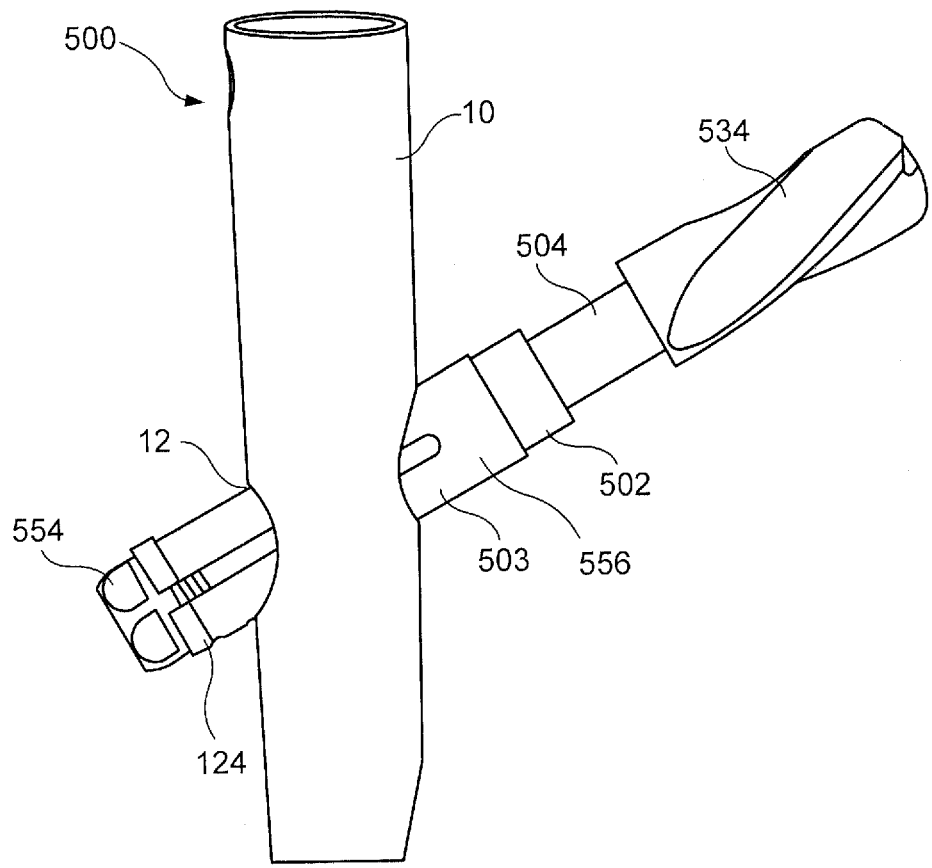
FIG. 20 shows a perspective view of a bone fixation system according to a fifth exemplary embodiment of the present invention.
Figure 21:
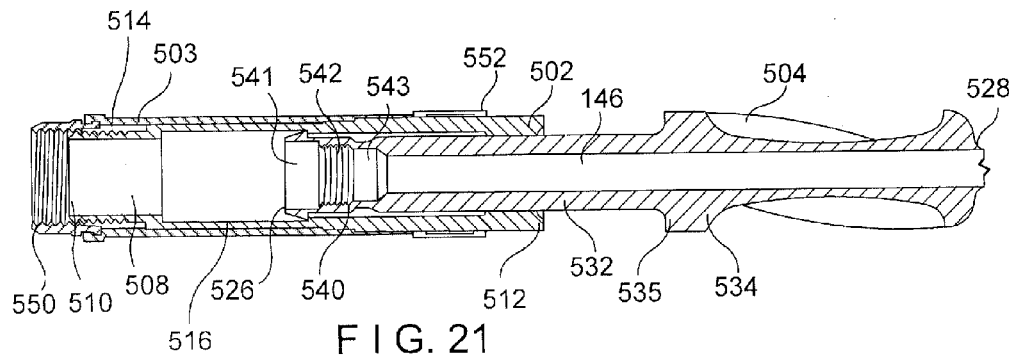
FIG. 21 shows a first partial cross-sectional view of the system of FIG. 20.
Figure 22:
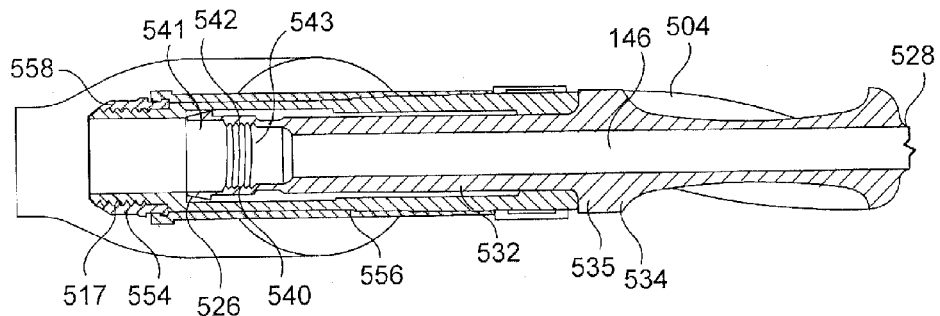
FIG. 22 shows a second partial cross-sectional view of the system of FIG. 20.
Figure 23:
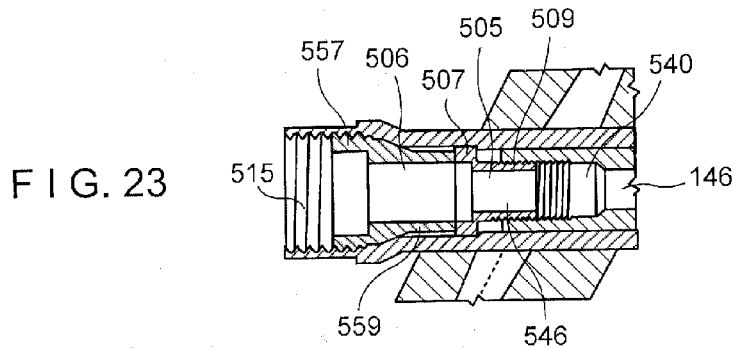
FIG. 23 shows a third partial cross-sectional view of the system of FIG. 20.
Figure 24:
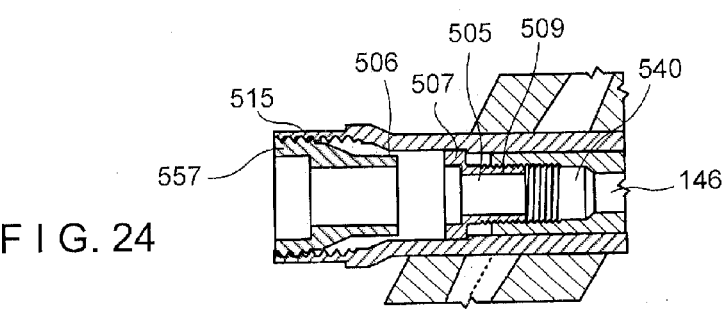
FIG. 24 shows a fourth partial cross-sectional view of the system of FIG. 20.

As shown in FIG. 18, a blocking device 450 for rotationally stabilizing the inner sleeve 406 relative to the outer sleeve 402 includes a pair of finger-like inserts 452 extending distally from a rotatable collar 454 surrounding a head portion 407 of a screw 406 so that the screw is rotatable relative thereto. The collar 454 includes an engaging structure 456 on an outer surface thereof corresponding to the structure 411 of the proximal end 410 of the outer sleeve 402. For example, the collar 454 may include circular toothwork along the outer surface thereof, corresponding to circular toothwork along the inner surface of the proximal end 410 of the outer sleeve 402. In use, as shown in FIG. 19, the blocking device 450 is inserted into the channel 446 of the inner sleeve 404 so that the finger-like inserts 452 extend over the flat surfaces of the proximal portion 430 of the inner sleeve 404 within a space between these flat surfaces and the inner surface of the channel 408 of the outer sleeve 402 to prevent rotation of the inner sleeve 404 relative to the finger-like inserts 452. The engaging structure 456 of the collar 454 engages the structure 411 of the inner sleeve 404 so that the collar 454 is prevented from rotating relative to the outer sleeve 402, while being permitted to move axially relative thereto. The screw 406, however, is rotatable relative to the collar 454 and finger-like inserts 452 to engage a threaded portion 448 of the channel 446. Thus, the screw 406 fixes the blocking device 450 to the inner sleeve 404 so that the inner and outer sleeves 404, 402 are prevented from rotating relative to one another, but permitted to move longitudinally relative to one another.

The inner sleeve 404 may be introduced through the nail 401 first with the outer sleeve 402 being slid thereover afterward or both sleeves 402 and 406 may be introduced together. After the outer sleeve 402 has been locked in a desired position by engaging the hemispherical projection 424 with the bayonet groove, the blocking device may be engaged by inserting the finger-like inserts 452 into the space between the flat surfaces of the inner sleeve 404 and the inner surface of the channel 408. The user then advances the screw 406 into the channel 446 by screwing it into the thread 448 via a driving tool engaging structure (e.g., hex opening 458) in the proximal end thereof.

As shown in FIGS. 20-24, a bone fixation system 500 according to another embodiment of the invention comprises an inner sleeve 502, outer sleeve 503, bone fixation element 504, a compression screw 505 and a limited collapse screw 506 which also acts as an end cap. The bone fixation element 504 extends from a proximal end 526 to a distal end 528 and comprises a substantially cylindrical portion 532 and a bone engaging structure 534 (e.g., thread, bladed, etc.). A length of the bone engaging structure 534 has an increased outer diameter 535 which is greater than an outer diameter of the inner sleeve 502. The bone engaging structure 534 extends over a predetermined length of the distal portion of the bone fixation nail 504 configured to extend out of the outer sleeve 502 and into direct contact with the bone in an operative configuration. A partially threaded opening 540 extends into the cylindrical portion 532 by a distance configured to permit threaded engagement with the compression screw 505. Specifically, the threaded opening 540 extends distally from the proximal end 526 and comprises a first non-threaded section 541 configured and dimensioned to receive an enlarged diameter head 507 of the first locking screw 505, a middle threaded portion 542 configured and dimensioned to engage threads of a shaft 626 of a connecting screw 620 and a distal non-threaded portion 543 opening into the central longitudinal channel 146 extending through the bone fixation element 504. The middle threaded portion 542 and the distal non-threaded portion 543 may have substantially the same diameter corresponding to an outer diameter of the shaft 509. The compression screw 505 further comprises a central longitudinal channel 546 configured to be longitudinally aligned with and open to the central longitudinal channel 146 of the bone fixation element 504 in an operative configuration to permit insertion of tools and other materials therethrough as described in greater detail earlier.

The substantially cylindrical portion 532 of the bone fixation element 504 is configured to be received at least partially within a channel 508 extending through the inner sleeve 502. Specifically, the inner sleeve 502 extends from a proximal end 510 to a distal end 512 and comprises a proximal threaded portion 514 at the proximal end and a smooth outer shaft portion 516 extending distally therefrom. The inner sleeve 502 is substantially conical so that a distal portion thereof has a greater diameter than a proximal portion, as will be described in greater detail with respect to the exemplary method of the invention. An outer diameter of the shaft portion 516 is smaller than a diameter of the increased outer diameter portion 535 of the element 504 to prevent proximal withdrawal of the helical blade 534 thereinto. An inner diameter of the shaft portion 516 receives the substantially cylindrical portion 532 with a substantial friction fit to prevent lateral movement of the element 504 therewithin. The proximal threaded portion 514 has a smaller inner and outer diameter than the shaft portion 516 to prevent retraction of the element 504 thereinto. The proximal threaded portion 514 is also provided with internal threads 515 configured to engage a head 557 of the limited collapse screw 506 and external threads 517 configured to engage the outer sleeve 503 as will be described in greater detail hereinafter.

The outer sleeve 503 extends from a proximal end 550 to a distal end 552 proximal of the distal end 512 of the inner sleeve 502. The outer sleeve 503 also comprises a proximal threaded portion 554 and a shaft portion 556 extending distally therefrom. The shaft portion 556 is configured to engage the inner sleeve 502 with a substantial friction fit. The proximal threaded portion 554 comprises internal threading 558 configured to threadedly engage the external threads 517 of the inner sleeve 502. The proximal threaded portion 554 and shaft portion 556 may be formed as separate elements attached to one another by a lip and groove engagement. Thus, the inner and outer sleeves 502, 503 and the fixation element 504 are fixed relative to one another without the need for a proximal locking element.

In accordance with an exemplary method according to the invention, as shown in FIGS. 25-28, an insertion instrument 600 is used to guide the bone fixation system 500 into the bone. The insertion instrument 600 comprises a first elongated tool 602 having an elongated cylindrical shaft 604 and a handle 606 at a proximal end thereof. The first elongated tool 602 is configured so that a distal end 608 of the shaft 604 contacts the proximal end 550 of the proximal threaded portion 554. The tool 602 engages the proximal threaded portion 554 such that rotation of the tool in, for example, a clockwise direction also rotates the threaded portion 554 over the threaded portion 514 of the inner sleeve 502, which causes the outer sleeve 503 to move distally relative to the inner sleeve 502, locking the system to the nail 10, as will be described in greater detail below. A second elongated tool 610 is configured and dimensioned to be received at least partially within the first elongated tool 602 and comprises an elongated substantially cylindrical shaft portion 612 and a handle 614 adjacent a proximal end thereof. A predetermined length of the shaft portion 612 is provided with external threading 616 configured to permit threaded engagement with a compression nut 618 provided thereover. A distal end of the second elongated tool 610 may be configured to engage the proximal end 526 of the fixation element 504 where, for example, the fixation element 504 includes a threaded bone engaging structure 534. The insertion instrument 600 also comprises an elongated connecting screw 620 insertable through the second elongated tool 610, the connecting screw 620 having an elongated cylindrical shaft 622 and a head 624 at a proximal end thereof. A distal end of the connecting screw 620 comprises a threaded portion 626 configured to threadedly engage the threaded portion 542 of the opening 540 of the bone fixation element 504.

Figure 25:
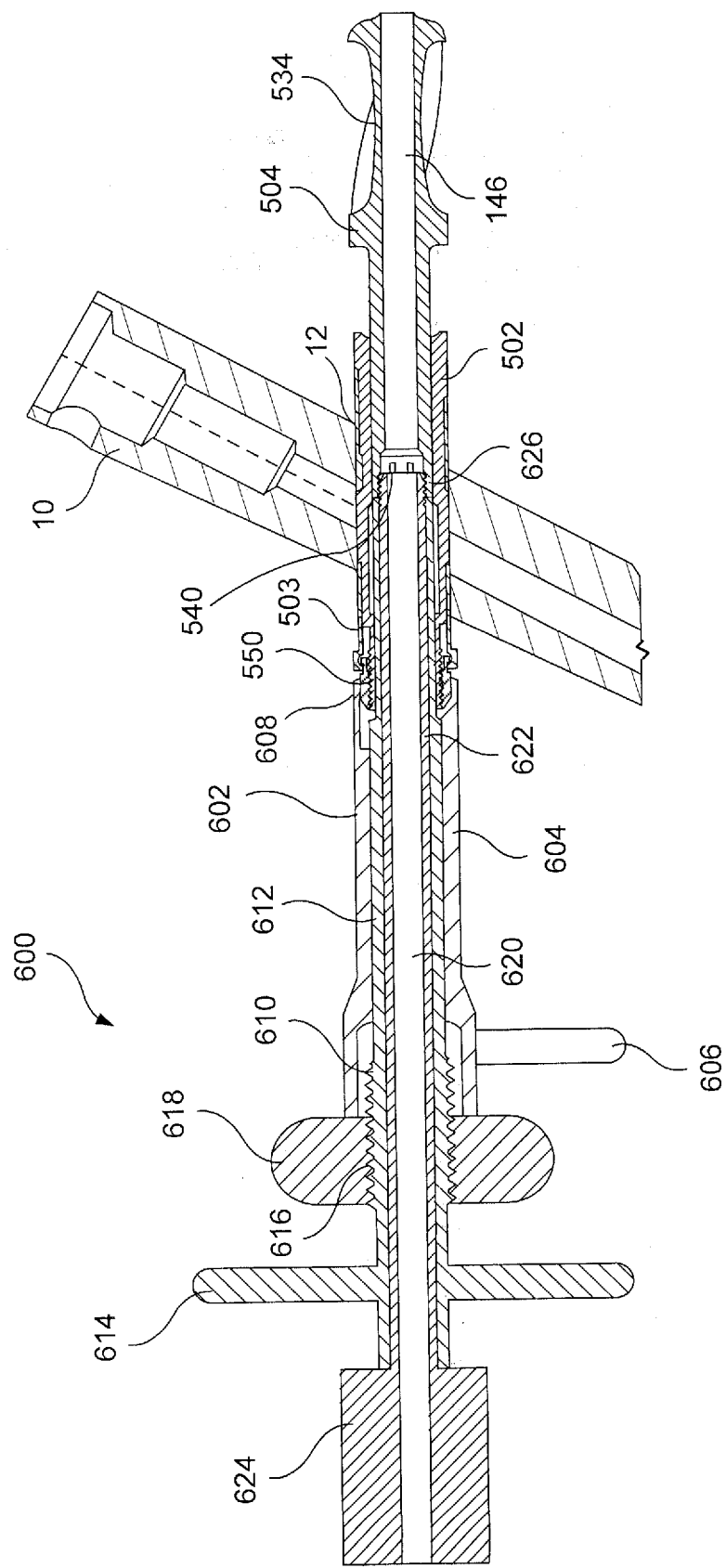
FIG. 25 shows a perspective view of an insertion tool according to a sixth exemplary embodiment of the present invention, which may be used for insertion of the bone fixation system of FIG. 20.

In a first step, the insertion instrument 600 is connected to the bone fixation system 500 as shown in FIG. 25. A distally directed force is then applied to the connecting screw 620 to cause advancement of the bone fixation element 504 and inner and outer sleeves 502, 503 through the intramedullary nail hole 12 and into the bone (not shown). Where the bone engaging structure 534 of the fixation element 504 is a blade, the fixation element 504 may be inserted through the bone by applying a distal force to the connecting screw 620 via a hammering force to the head 624 thereof. Where the bone engaging structure 534 is a thread, the user may rotate the handle 614 to rotate the tool 610 in, for example, a clockwise direction to rotate the bone fixation element 504 into the bone. In the insertion configuration of FIG. 25, the inner sleeve 502 may be positioned so that the distal end 512 thereof is positioned distally of the distal end 552 of the outer sleeve 503. The tool 602 is rotated to move the outer sleeve 502 distally relative to the inner sleeve 502. The relative longitudinal movement of the inner sleeve 502 relative to the outer sleeve 503 causes a distal conical portion of the inner sleeve 502 to apply a radially expansive force to the outer sleeve 503, locking the system 500 within the nail 10. The compression nut 618 may then be rotated by a required distance to add compression to the bone. Rotation of the compression nut 618 causes the increased outer diameter portion 535 of the bone engaging structure 534 and the distal ends of the inner and outer sleeves 502, 503 to move closer to one another as shown in FIG. 28. Once the bone fixation element 504 has been moved to a target position, the insertion instrument 600 is removed and the first locking screw 505 has been inserted into the opening 540 to a first target depth which may correspond to a depth of the bone fixation element 504 within the bone (not shown). The second locking screw 506 is then inserted into the inner sleeve 502 until external threads of the head 557 engage the internal threads 558 of the inner sleeve 502. The second locking screw 506 is screwed distally into the inner sleeve 502 until a distal end thereof contacts the head 507 of the first locking screw 505. The first and second locking screws 505, 507 thus lock a position of the bone fixation element 504 within the bone while permitting lateral movement thereof within a desired range as described in greater detail earlier.

As shown in FIGS. 29-32, a bone fixation system 700 according to yet another embodiment of the invention comprises a bone fixation nail 704 formed substantially similarly to the bone fixation nails of earlier embodiments. The bone fixation nail 704 comprises an elongated substantially cylindrical portion 732 having a helical blade 734 at a distal end thereof. An opening 740 extends into a proximal end 726 of the bone fixation nail 704 to a predetermined depth and comprises a proximal threaded portion 742 and a distal non-threaded portion 744. The opening 740 is configured and dimensioned to threadedly engage a locking screw 706. The system 700 also comprises a substantially cylindrical outer sleeve 702 extending from a proximal end 710 to a distal end 712 and having a central longitudinal channel 708 extending therethrough. The distal end 712 comprises an abutment 703 extending into the channel 708 a distance selected to prevent a head 707 of the locking screw 706 from moving distally therepast. An internal threaded portion 705 extends into the proximal end 710 by a distance selected to permit threaded engagement with an end cap 750, as will be described in greater detail hereinafter.

The exemplary bone fixation system 700 may be inserted into a bone (not shown) using the insertion instrument 600' formed substantially similarly to the insertion instrument 600 described earlier, and like elements are referenced with like reference numerals. Specifically, the insertion instrument 600' comprises a first elongated tool 602' having the elongated cylindrical shaft 604 and a handle 606' at a proximal end thereof. The handle 606', according to this embodiment, is circumferential and extends around an entire circumference of the proximal end of the first elongated tool 602'. Alternatively, the handle 606' may be a multi-part handle having multiple gripping portions distributed about the circumference of the first elongated tool 602'. The distal end 608 of the shaft 604 is configured to contact the proximal end 710 of the outer sleeve 702. The distal end 608 may be sized and shaped to engage a correspondingly shaped (e.g., hexagonal) proximal end 710 of the outer sleeve 702. A second elongated tool 610' is configured and dimensioned to be received at least partially within the first elongated tool 602' and comprises the elongated substantially cylindrical shaft portion 612 and a handle 614 adjacent a proximal end thereof. A predetermined distal length of the shaft portion 612 includes external threading 616' configured to permit threaded engagement with the internal threaded portion 705 of the outer sleeve 702. The elongated compression instrument 620 is insertable through the second elongated tool 610' and comprises the elongated cylindrical shaft 622 and a head 624 at a proximal end thereof. A distal end of the elongated compression instrument 620 is configured to engage a head portion of the locking screw 706.

Figure 29:
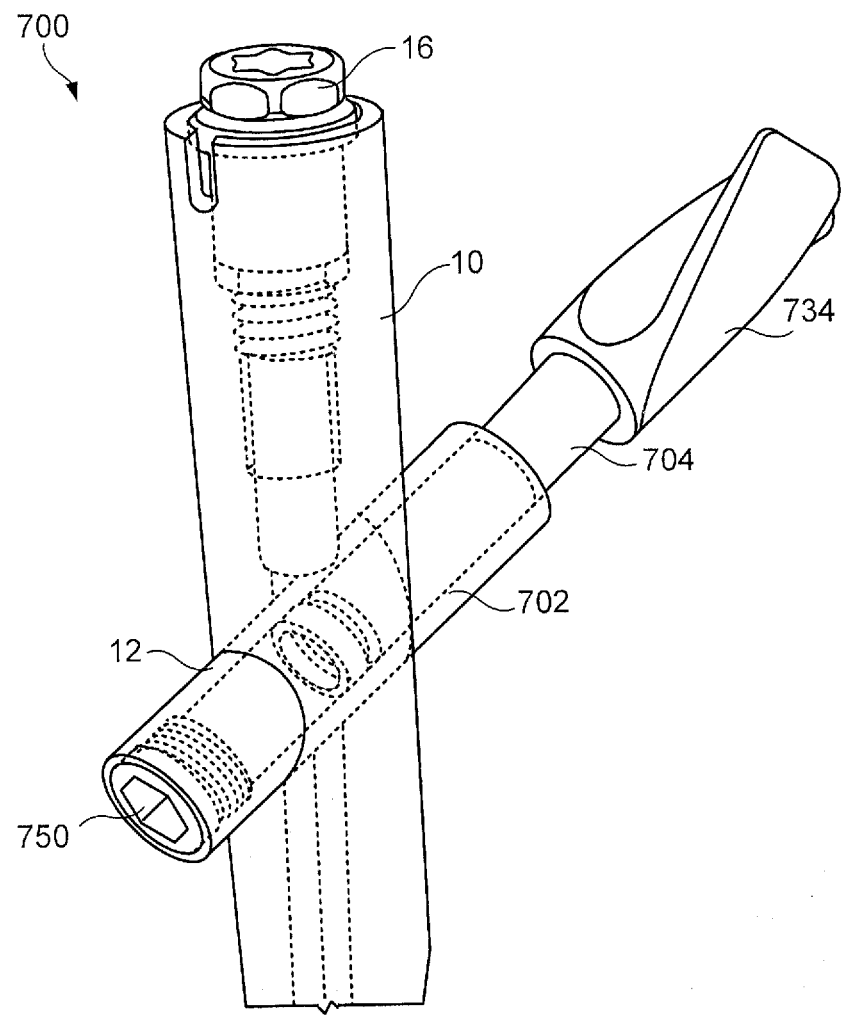
FIG. 29 shows a perspective view of a bone fixation system according to a seventh exemplary embodiment of the present invention.
Figure 33:
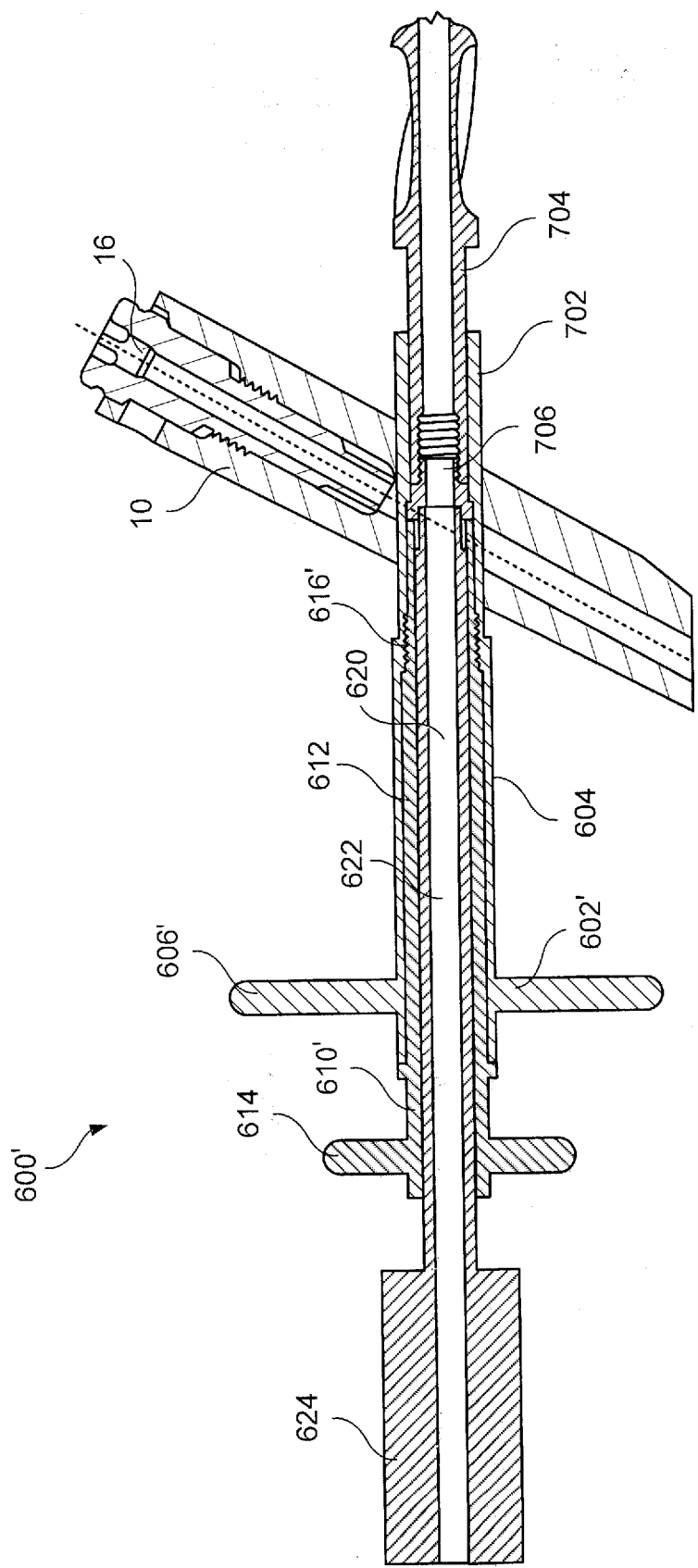
FIG. 33 shows a perspective view of an insertion tool according to an eighth exemplary embodiment of the present invention, which may be used for insertion of the bone fixation system of FIG. 29.
Figure 34:
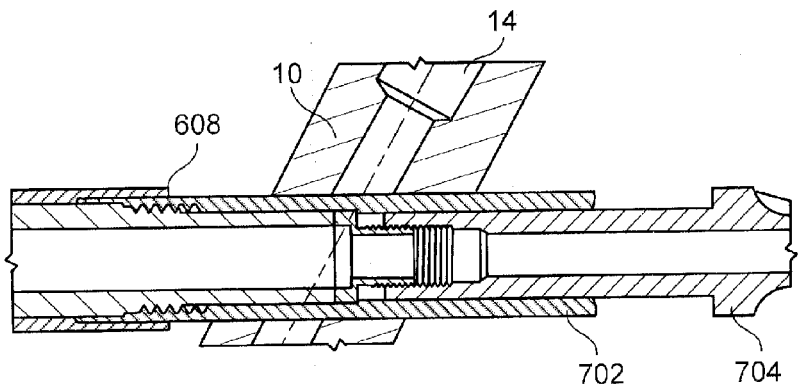
FIG. 34 shows a first partial cross-sectional view of the tool of FIG. 33 with the system of FIG. 28.
Figure 35:
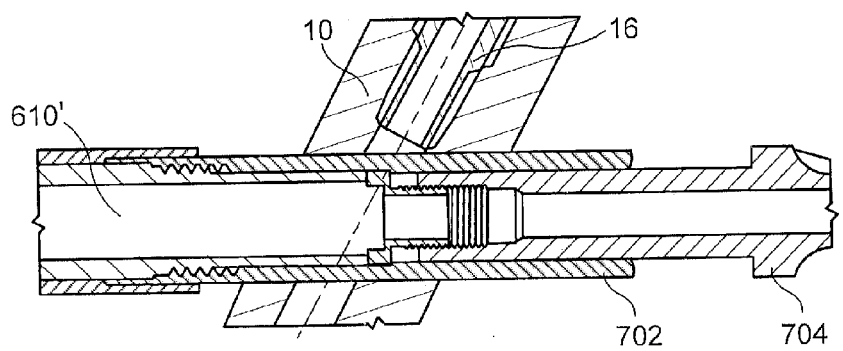
FIG. 35 shows a second partial cross-sectional view of the tool of FIG. 33 with the system of FIG. 28.
Figure 36:
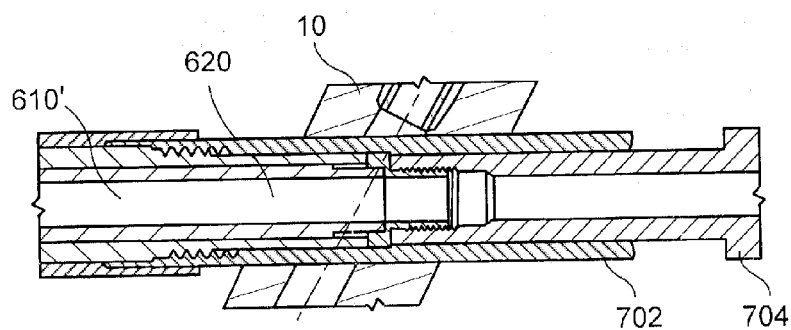
FIG. 36 shows a third partial cross-sectional view of the tool of FIG. 33 with the system of FIG. 28.
Figure 37:
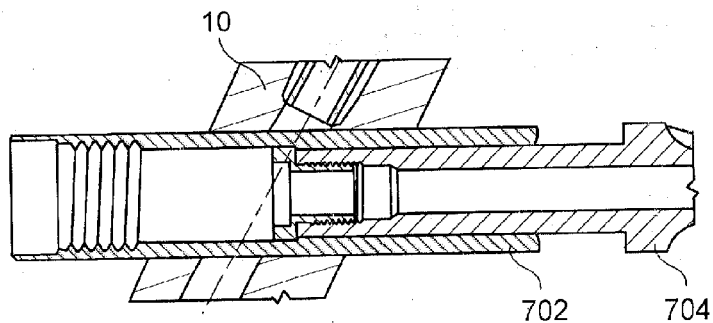
FIG. 37 shows a fourth partial cross-sectional view of the tool of FIG. 33 with the system of FIG. 28.
Figure 38:
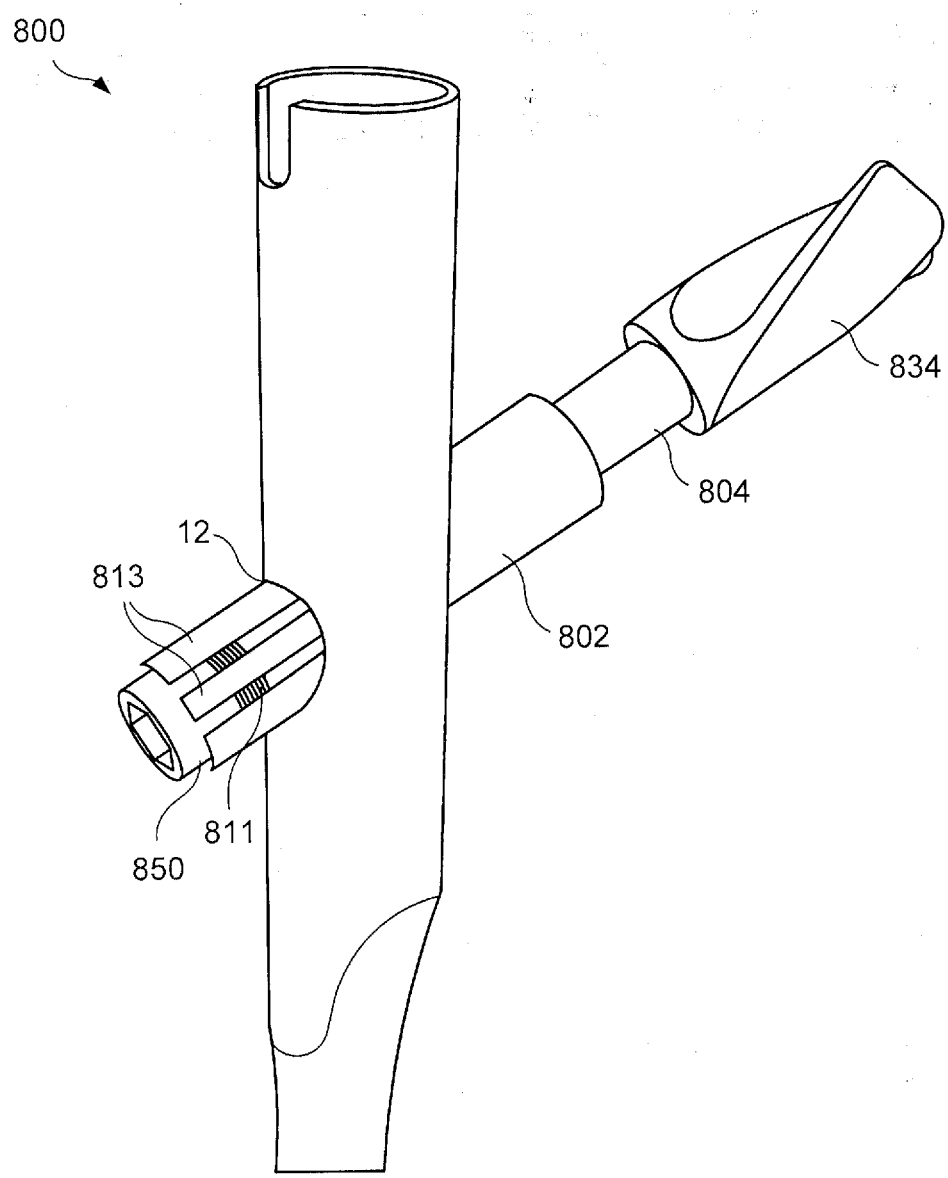
FIG. 38 shows a perspective view of a bone fixation system according to a ninth exemplary embodiment of the present invention.
Figure 39:
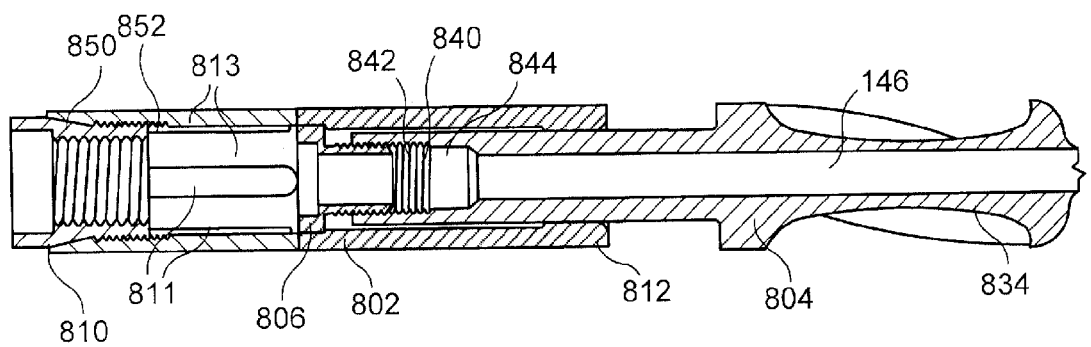
FIG. 39 shows a first partial cross-sectional view of the system of FIG. 38.

In accordance with an exemplary method according to the invention, the insertion instrument 600' is positioned with the bone fixation system 700 as shown in FIG. 33. As shown in FIG. 34, the second elongated tool 610' is then used to advance the bone fixation nail 704 into the bone. Specifically, if the bone fixation nail 704 comprises the blade 734, a distal axial force is applied to the second elongated tool 610'. If the bone fixation nail is a threaded screw, the handle 606' may be rotated to cause rotation of the threaded screw distally into the bone. A transverse locking cap 16 is then inserted into the locking screw hole 14 of the intramedullary nail 10 to apply a transverse locking force to the outer sleeve 702 to lock a position thereof. As shown in FIG. 36, the elongated compression element 620 may then be inserted through the second elongated tool 610' to add compression. Specifically, the elongated compression element 620 may be rotated relative to the second elongated tool 610' to rotate the screw 706, which pulls the fixation element 704, which is threadedly engaged thereto, proximally. Once a desired compression has been achieved, the insertion instrument 600' may be removed from the bone fixation device 700, as shown in FIG. 37. The end cap 750 may then be inserted into the outer sleeve 702 as shown in FIG. 29. As described in greater detail in earlier embodiments, the bone fixation nail 704 may be permitted to move laterally within the outer sleeve 702 by approximately 10 mm from the configuration of FIG. 30 to the configuration of FIG. 31. If it is desired to restrict this movement to a smaller range of movement, an endcap 750' with a greater length may be inserted into the outer sleeve 702. Additionally, as also disclosed in earlier embodiments, the endcaps 750, 750', locking screw 706 and bone fixation nail 704 may all comprise central longitudinal channels extending therethrough and configured to align with one another in an operative implanted configuration to permit the insertion of medical tools/or other materials therethrough.

As shown in FIGS. 38-41, a bone fixation system 800 according to another embodiment of the invention comprises a bone fixation nail 804 having a substantially cylindrical portion 832 and a distal helical blade 834. An opening 840 is provided on a proximal end thereof and comprises a proximal threaded portion 842 and a distal non-threaded portion 844 open to the central longitudinal channel 146. The opening 840 is configured and dimensioned to receive a compression screw 806 therein. The compression screw 806 according to this embodiment has an increased diameter head 807 and a threaded shaft 809 configured to threadedly engage the proximal threaded portion 842.

Figure 40:
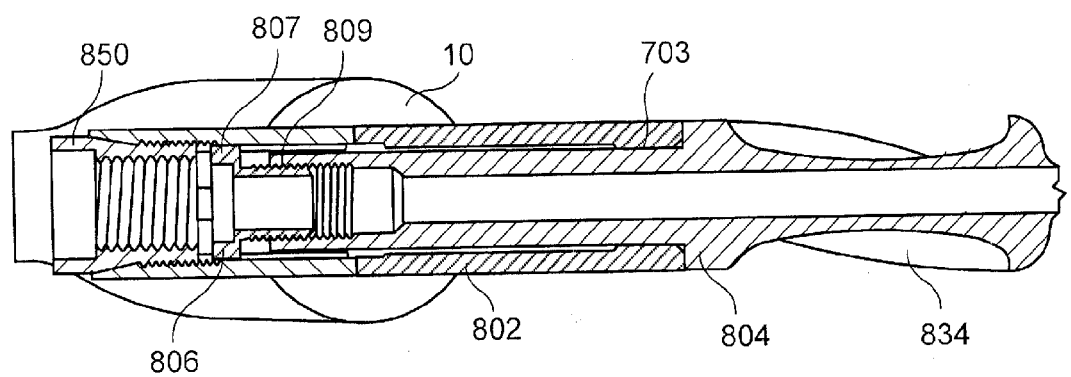
FIG. 40 shows a second partial cross-sectional view of the system of FIG. 38.
Figure 41:
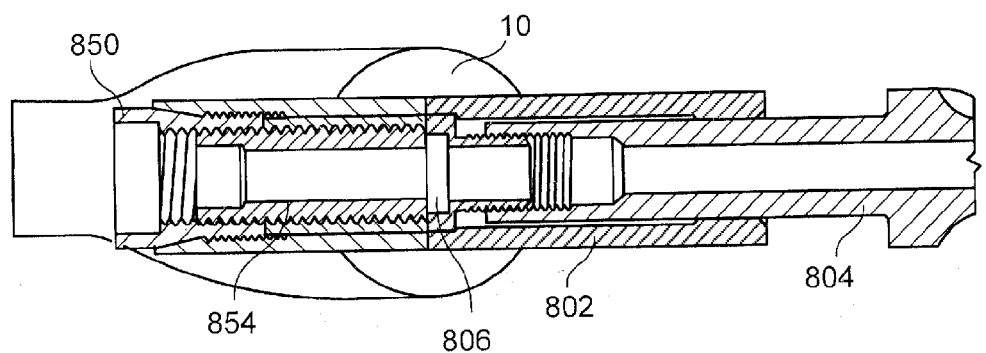
FIG. 41 shows a third partial cross-sectional view of the system of FIG. 38.

The bone fixation system 800 also comprises a substantially cylindrical outer sleeve 802 extending from a proximal end 810 to a distal end 812, the distal end 812 comprising the increased thickness portion 703 to prevent the compression screw 806 from moving distally therepast. A proximal portion of the outer sleeve 802 comprises a plurality of slots 811 defining a respective number of arms 813 which may deflect radially outward upon application of a radially expansive force thereto. An exemplary insertion method for the bone fixation system 800 is substantially similar to methods disclosed earlier, wherein the bone fixation nail 804 and outer sleeve 802 are inserted through an intramedullary nail hole 12 to a target depth so that the arms 813 are located proximally of the intramedullary nail hole 12. The locking screw 806 is at least partially threaded into the opening 840 during insertion. Once the nail 804 and outer sleeve 802 have been inserted to a target depth, an end cap 850 is screwed into the proximal end 810 to threadedly engage internal threads 852 of the outer sleeve 802 to partially radially expand the outer sleeve 802 and thus aid in locking thereof within the bone, as those skilled in the art will understand. In this configuration, the bone fixation nail 804 may be permitted to move axially within the outer sleeve by approximately 10 mm., as described in greater detail earlier. As would be understood by those skilled in the art, this movement may be eliminated or limited by inserting a locking cap 854 through the end cap 850 so that a distal end 856 thereof abuts the head 807 of the locking screw 806, as shown in FIG. 40. The locking cap 854 may also comprise a central longitudinal channel 858 extending longitudinally therethrough to permit insertion of tools or other materials therethrough, as described in greater detail earlier.

Figure 42:
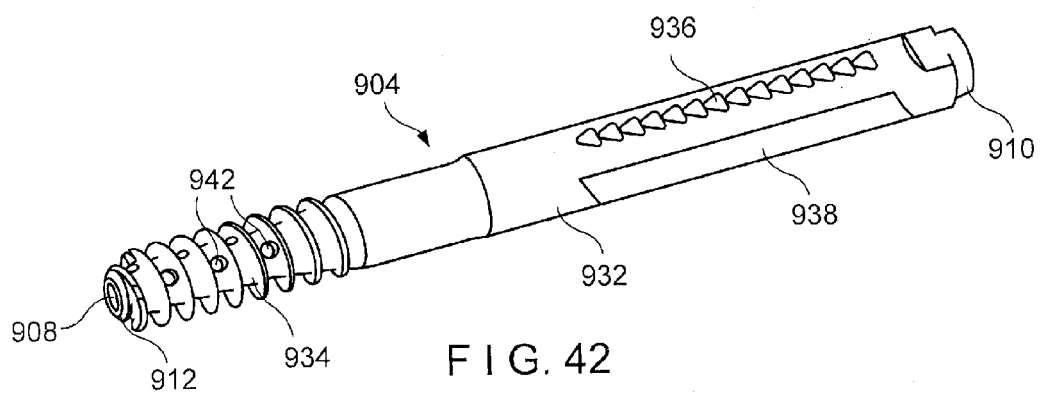
FIG. 42 shows a first perspective view of a bone fixation device according to a tenth exemplary embodiment of the present invention.
Figure 43:
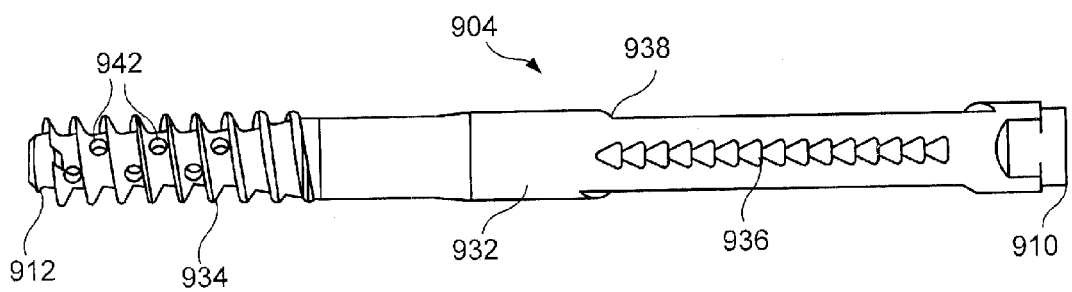
FIG. 43 shows a second perspective view of the element of FIG. 42.
Figure 44:
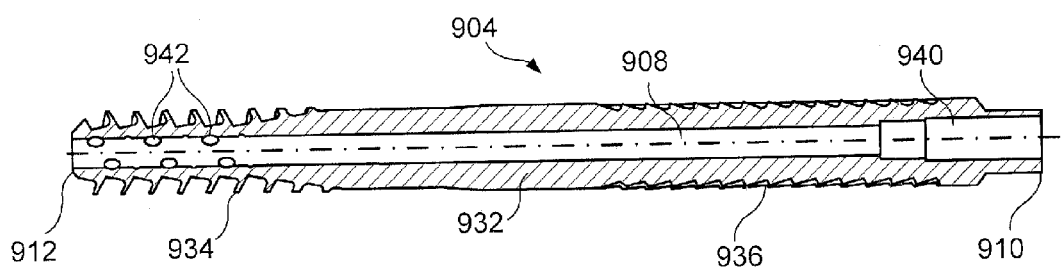
FIG. 44 shows a third perspective view of the element of FIG. 42.
Figure 45:
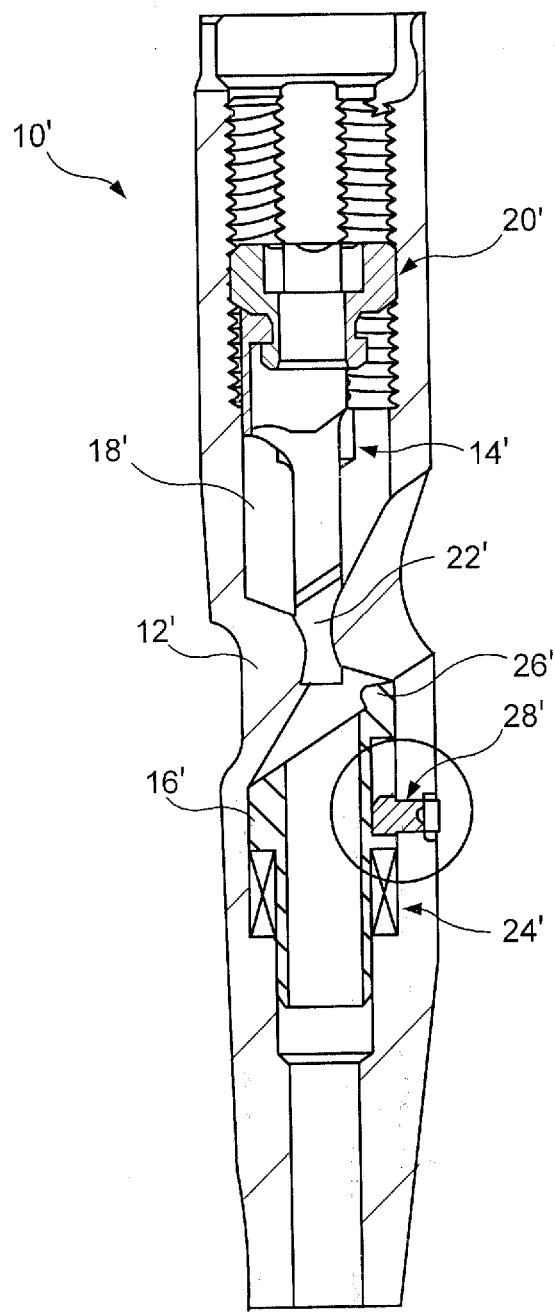
FIG. 45 shows a longitudinal cross-sectional view of an intramedullary nail to be utilized with the bone fixation element of FIG. 42
Figure 46:
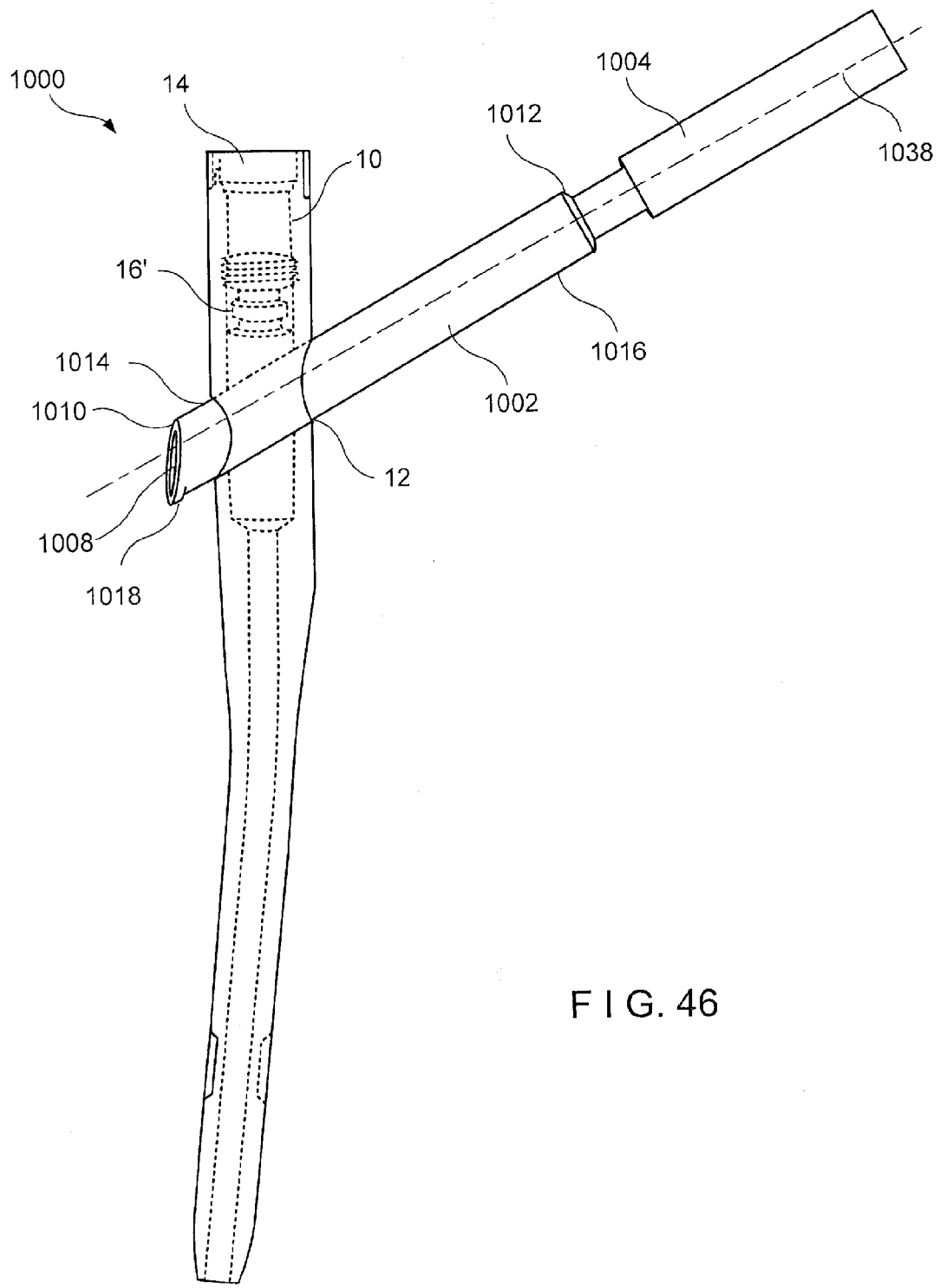
FIG. 46 shows a first perspective view of a bone fixation device according to an eleventh exemplary embodiment of the present invention.
Figure 47:
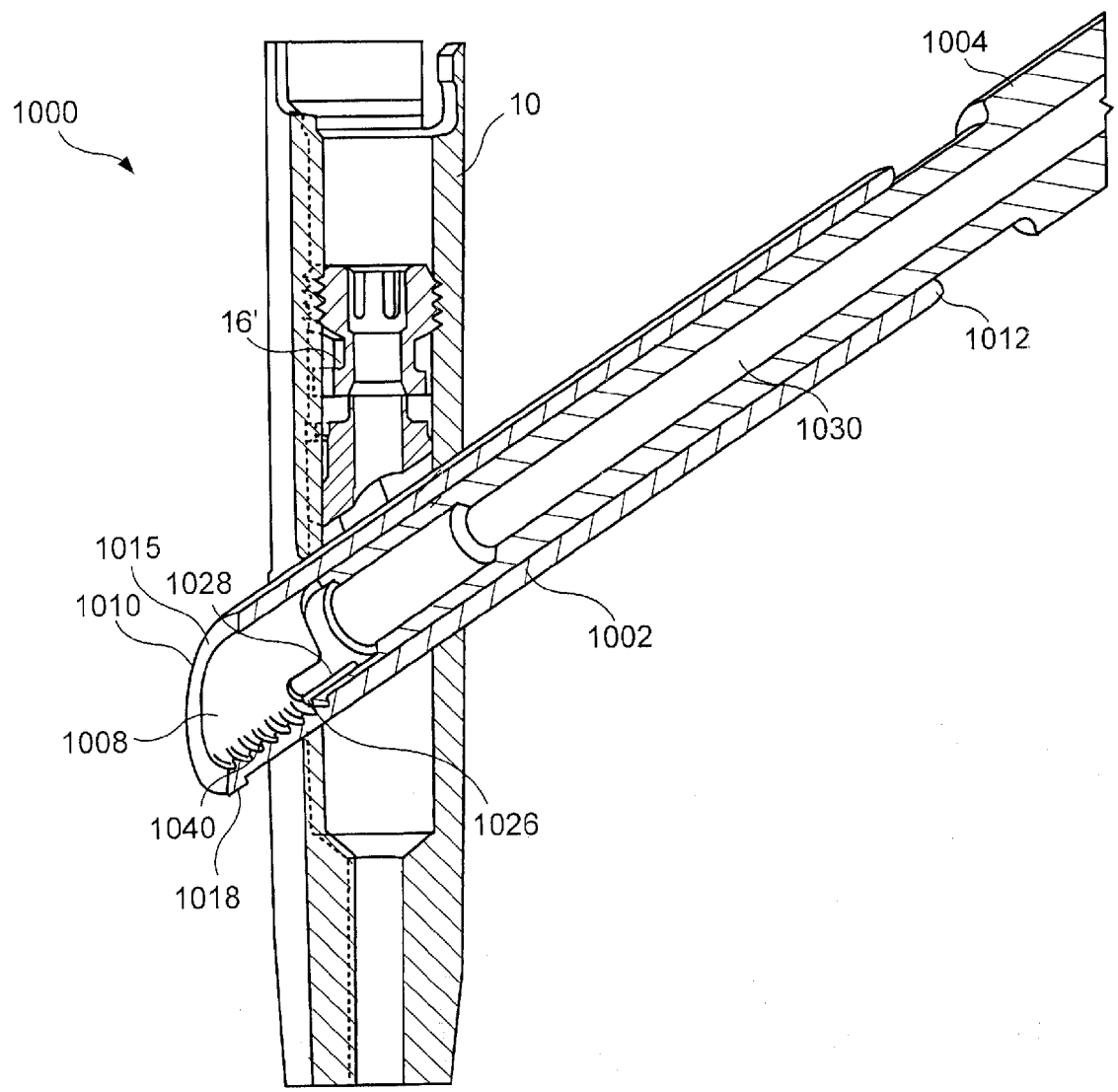
FIG. 47 shows a partial cross-sectional view of the element of FIG. 46.

A bone fixation system 900 according to another exemplary embodiment of the invention comprises a bone fixation element 904, as shown in FIGS. 42-44, sized and shaped for insertion through a hole 12' of an intramedullary nail 10', as shown in FIG. 45. Similarly to the nail 10 described above, the intramedullary nail 10' extends along a longitudinal axis and the hole 12' extends through the nail 10' at an angle relative to the longitudinal axis. The intramedullary nail 10', however, further comprises a lock prong 14' arranged within a channel 18' of the nail 10° proximally of the hole 12' and a plunger 16' arranged within the channel 18' of the nail 10' distally of the hole 12'. The lock prong 14' includes a pair of arms 22', each of which are positioned on opposing sides of the hole 12'. The lock prong 14' may be moved distally within the nail 10' such that the arms 22' extend into the hole 12' to engage cutouts 938 of the bone fixation element 904, as will be described in further detail below. The lock prong 14' is moved longitudinally within the channel 18' via a lock drive 20' coupled to a proximal end of the lock prong 14'. The lock drive 20' is threadedly engaged to an inner surface of the channel 18' and rotationally engaged to the proximal end of the lock prong 14' such that rotation of the lock drive 20' in a first direction relative to the nail 10' moves the lock prong 14' distally within the channel 18' such that the arms 22' extend into the hole 12'. Rotation of the lock drive 20' in a second direction moves the lock prong 14' proximally relative to the nail 10'.

The plunger 16' includes a protrusion 24' extending proximally therefrom. The plunger 16' is movable between a first and second position via a spring 24', which biases the plunger 16' in the first position. In the first position the protrusion 26' extends into the hole 12' while in the second position the plunger 16' is moved distally relative to the nail 10' so that the protrusion 16' does not extend into the hole 12'. The plunger 16' is prevented from moving beyond a predetermined longitudinal range via a pin 28' which fixes the plunger 16' to nail 10'. The protrusion 16' is sized and shaped to engage a serrated portion 936 of the bone fixation element 904, as will be described in greater detail below.

The bone fixation element 904 includes a cylindrical elongated portion 932 and a bone engaging distal portion 934. The distal portion 934 may include bone engaging structures such as, for example, threads or blades. The element 904 extends from a proximal end 910 to a distal end 912. The elongated portion 932 comprises a serrated edge portion 936 extending along a predetermined length thereof at an angle substantially parallel to a longitudinal axis of the nail 904. In another embodiment, a pair of the serrated portions 936 may be provided and separated from one another by approximately 180°, as shown in FIG. 44. The serrated portion 936 is cut to engage the protrusion 26' of the plunger 16' such that the bone fixation element 904 is permitted to be inserted through the hole 12' and into a head portion of a bone, but prevented from migrating medially therethrough.

The element 904 may also comprises a pair of longitudinal cutouts 938 also separated from one another by approximately 180° and separated from respective ones of the serrated portions by approximately 90°. The cutouts 938 are engaged by the arms 22' of the lock prong 14' when the lock prong 14' is moved so that the arms 22' extend into the hole 12'. Engagement between the arms 22' and the longitudinal cutouts 938 prevents the bone fixation element 904 from rotating relative to the nail 10' and permits a medial/lateral sliding within a predefined range of motion defined by proximal and distal ends of the cutout 938.

The distal portion 934 may be threaded or include blades for engaging a bone into which the bone fixation element is inserted. The distal portion 934 may also include openings 940 extending thereinto and open to the channel 908. The openings 942 may be disposed over the distal portion 934 in any configuration without deviating from the scope of the invention (e.g., staggered, longitudinally aligned, etc.) and may be used to permit injection of a material (e.g. a bone strengthening material) into the bone after implantation. An opening 940 may extend into the proximal end 910 of the nail 904 by a predetermined distance to permit engagement with a locking screw (not shown), as described in greater detail in earlier embodiments.

FIGS. 46-49 depict a bone fixation system 1000 according to another exemplary embodiment of the invention. The bone fixation system comprises a bone fixation nail 1004 formed substantially similarly to the bone fixation nails of earlier embodiments. The bone fixation system 1000 also comprises an outer sleeve 1002 configured to receive the bone fixation nail 1004 therethrough and a locking screw 1006 configured to be at least partially inserted into the outer sleeve 1002. The outer sleeve 1002 comprises a longitudinal channel 1008 extending therethrough along a longitudinal axis 1038 from a proximal end 1010 to a distal end 1012. The longitudinal channel 1008 may be shaped as a substantially elliptical or circular cylinder without deviating from the scope of the invention. The outer sleeve 1002 may also be provided with flats 1015 along first and second longitudinal side walls 1014, 1016 to provide further rotational stability of the outer sleeve 1002 relative to the intramedullary nail 10, as is also described in earlier embodiments. The first longitudinal side wall 1014 has a first length and the second longitudinal side wall 1016 has a second length greater than the first length such that the proximal end 1010 is substantially oblique. In an exemplary embodiment a difference in length between the opposing first and second side walls 1014, 1016 is approximately equal to a difference in length between the first and second side walls 1014', 1016' of the locking screw 1006 to permit flush engagement therewith when in an operative configuration. The second side wall 1016 further comprises a barb 1018 adjacent the proximal end 1010 of the outer sleeve 1002. The barb 1018 protrudes from the outer sleeve 1002 by a length sufficient to permit engagement thereof with a peripheral wall of the intramedullary nail hole 12, as described in greater detail in earlier embodiments.

Figure 48:
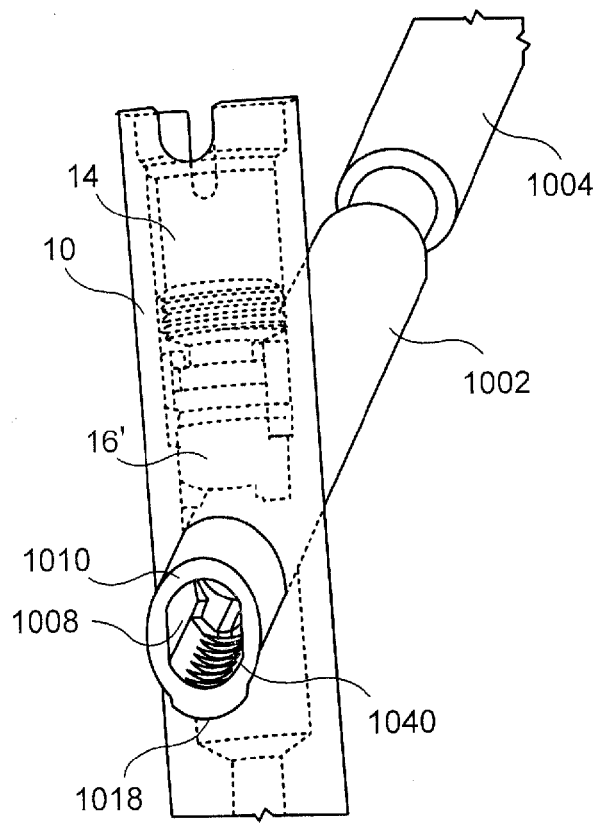
FIG. 48 shows a third perspective view of the element of FIG. 46.
Figure 49:
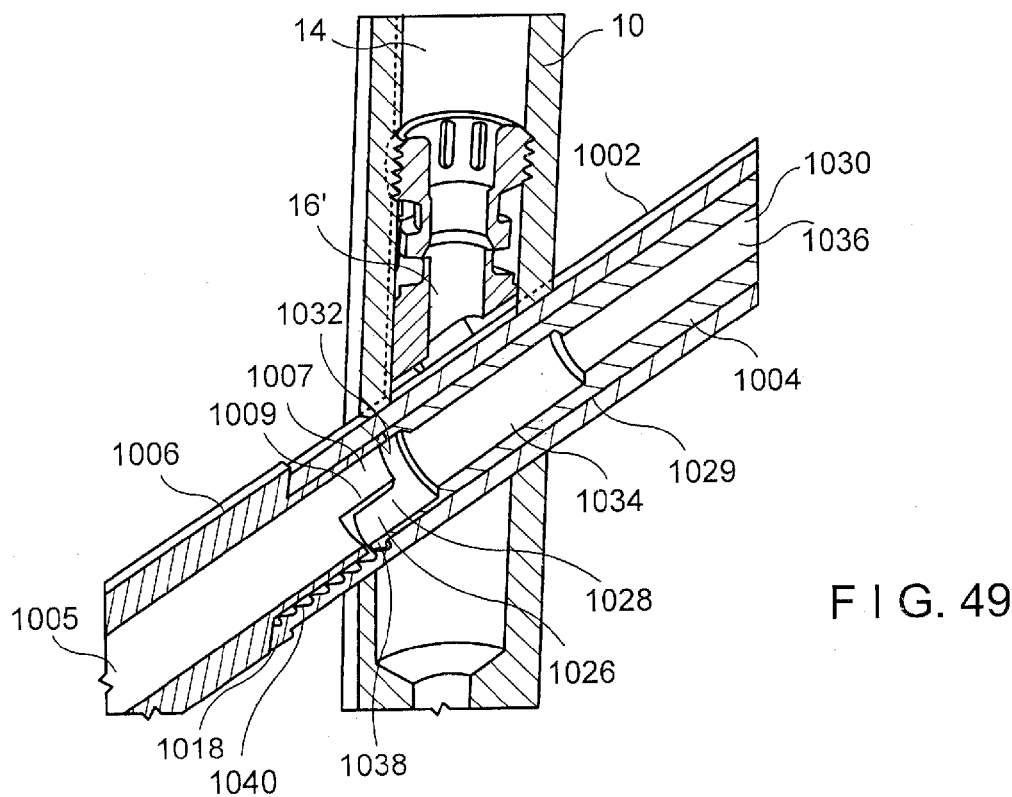
FIG. 49 shows a fourth perspective view of the element of FIG. 46.

The bone fixation element 1004 extends from a proximal end 1026 to a distal end (not shown). The proximal end 1026 of the bone fixation element 1004 is formed with a tab 1028 having a shape complementary that of a recess 1009 formed on a protruding head 1007 of the locking screw 1006. Specifically, as shown in FIG. 49, the tab 1028 extends proximally away from the bone fixation element 1004 along a side wall 1029 by a predetermined distance. The locking screw 1006 is provided with a recess 1009 positioned to receive the tab 1028 therewithin in an operative configuration. The bone fixation element 1004 also comprises a longitudinal channel 1030 extending longitudinally therethrough from the proximal end 1026 to the distal end (not shown). A proximal portion 1032 of the longitudinal channel 1030 is formed with a diameter substantially similar to the diameter of a channel 1005 extending through the locking screw 1006 to permit a transfer of a desired medical tool or injectable material from the locking screw 1006 to the bone fixation element 1004 and subsequently into a target region of a bone without interference. The diameter of the channel 1030 of the bone fixation element 1030 decreases incrementally in a distal direction via an intermediate channel portion 1032 and a distal channel portion 1034, as shown in FIG. 49. The tab 1028 of the bone fixation element 1004 further comprises a notch 1038 formed substantially similarly as the barb 1018, the notch 1038 being configured to ratchedly engage grooves 1040 provided on a proximal portion of the channel 1008 of the outer sleeve 1002. The exemplary embodiment of FIGS. 46-49 provides an integrated ratcheting mechanism to permit telescoping movement of the bone fixation element 1004 relative to the outer sleeve 1002, preventing and/or minimizing medial migration of the bone fixation element 1004 while also reducing frictional wear thereon. As discussed in greater detail in earlier embodiments, a distal portion (not shown) of the bone fixation element 1004 may be provided with a helical blade, threading, notches, or any other shape to facilitate bone fixation when implanted to a target trochanteric position.

The locking screw 1006 also comprises a notch (not shown) adjacent the groove 1009, the notch also being configured to ratchedly engage the grooves 1040 of the outer sleeve 1002, as will be described in greater detail below.

In accordance with an exemplary method for the bone fixation system 1000, a fractured or otherwise damaged bone (not shown) is brought into corrective alignment and the intramedullary nail 10 is inserted into a medullary cavity thereof to a target position and orientation therein in any known manner. The bone fixation element 1004 is then inserted through the intramedullary nail hole 12 to a target depth until an increased diameter distal portion has moved distally out of the intramedullary nail 12. The outer sleeve 1002 is then inserted through the intramedullary nail hole until the notch 1038 of the bone fixation element 1004 engages the threads 1040 of the outer sleeve 1002, as shown in FIG. 48. An intramedullary nail locking screw 16' may then be inserted into the locking screw hole 14 of the intramedullary nail 10 to lock a position of the outer sleeve 1002 and prevent lateral migration thereof (e.g., during temporary extraction). Once the outer sleeve 1002 and the bone fixation element 1004 have been positioned as desired within the hole 12, the locking screw 1006 is inserted thereinto so that the recess 1009 lies flush against the tab 1028 and so the notch (not shown) thereon lockingly engages the grooves 1040. The locking screw 1006 may be provided with markings to aid in insertion thereof into the outer sleeve 1002 at a desired angle to ensure proper placement against that bone fixation element 1004. In this configuration, the locking screw 1006 is prevented from being retracted proximally out of the intramedullary nail hole 12 due to engagement of the notch (not shown) with the grooves 1040. As with earlier embodiments, the bone fixation system 1000 permits lateral movement of the bone fixation element 1004 within the outer sleeve 1002 by approximately ±10 mm.

It will be apparent to those skilled in the art that various modifications and variations may be made in the structure and the methodology of the present invention, without departing from the spirit or scope of the invention. Thus, it is intended that the present invention cover modifications and variations of the invention provided that they come within the scope of the appended claims and their equivalents.

What is claimed is:

1. A device for bone fixation, comprising:
   a bone fixation nail extending from a proximal end to a distal end, the distal end having a helical structure configured to engage a bone, the proximal end having a first opening extending thereinto;
   a first sleeve configured for insertion over a proximal portion of the bone fixation nail and through an intramedullary nail hole, the first sleeve permitting the bone fixation nail to move axially therewithin within a predetermined range of movement;
   a first threaded connector attached to the proximate end of the bone fixation nail, the first threaded connector having a second opening extending therethrough, and a lip on a distal end of the first threaded connector to engage a groove provided in the bone fixation nail; and a locking screw configured to limit movement of the bone fixation nail relative to the first sleeve, the locking screw configured to lockingly engage the first and second openings and having a head and a threaded shaft extending distally therefrom.

2. The device of claim 1, further comprising a first radial abutment located adjacent a distal end of the first sleeve configured to prevent proximal retraction of the first sleeve out of the intramedullary nail hole therepast.

3. The device of claim 2, wherein the first radial abutment is radially compressible against the first sleeve during distal advancement through the intramedullary nail hole.

4. The device of claim 2, further comprising a second radial abutment located adjacent a proximal end of the first sleeve configured to prevent distal movement of the first sleeve into the intramedullary nail hole therepast.

5. The device of claim 1, further comprising a second sleeve provided over the first sleeve and axially moveable relative thereto.

6. The device of claim 1, wherein a proximal portion of the first sleeve comprises a plurality of longitudinal slots defining a respective number of radially deflectable arms.

7. The device of claim 1, further comprising a second threaded connector configured to threadedly engage the first threaded connector and having an outer diameter substantially equivalent to an outer diameter of the proximal portion of the bone fixation nail.

8. The device of claim 7, wherein a distal face of the second threaded connector comprises a treated surface configured to engage a respectively treated surface on the proximal portion of the bone fixation nail.

9. The device of claim 8, wherein the treated surface is one of serrated and notched.

10. The device of claim 7, wherein the second threaded connector comprises a pair of slots defining a radially protruding tab extending thereoutof for engaging an insertion instrument.

11. The device of claim 1, wherein a diameter of the head of the locking screw is one of greater than and equal to an inner diameter of the first sleeve.

12. The device of claim 1, wherein the bone fixation nail comprises a central longitudinal channel extending therethrough and being open at proximal and distal ends thereof to permit insertion of a tool therethrough.

13. The device of claim 12, wherein the helical structure comprises a first opening extending thereinto and open to the central longitudinal channel to permit one of an infusion and a withdrawal of a material therethrough.

14. The device of claim 1, wherein a proximal end of the helical structure comprises an increased diameter portion to prevent proximal retraction of the bone fixation nail into the first sleeve therepast.

15. The device of claim 1, wherein the helical structure is one of a helical blade and a threaded portion.

16. The device of claim 1, wherein a proximal portion of the bone fixation nail comprises a first serrated portion extending along a first longitudinal side wall thereof.

17. The device of claim 1, further comprising a notch located on the proximal end of the bone fixation nail, the notch being configured to ratchetly engage a grooved portion of the first sleeve to lock a position of the bone fixation nail relative to the outer sleeve.

18. The device of claim 17, further comprising a second notch located on the distal end of the locking screw, the second notch configured to ratchetly engage the grooved portion of the first sleeve to lock a position of the locking screw relative to the outer sleeve.

19. A device for bone fixation, comprising:
a bone fixation nail extending from a proximal end to a distal end, the distal end having a helical structure configured to engage a bone, the proximal end having an opening extending thereinto;
a first sleeve configured for insertion over a proximal portion of the bone fixation nail and through an intramedullary nail hole, the first sleeve permitting the bone fixation nail to move axially therewithin within a predetermined range of movement, wherein the first sleeve is substantially conical in shape so a distal end thereof has a greater diameter than a proximal end thereof; and
a locking screw configured to limit movement of the bone fixation nail relative to the first sleeve, the locking screw configured to lockingly engage the openings in the bone fixation nail and having a head and a threaded shaft extending distally therefrom.

20. The device of claim 19, wherein the proximal end of the first sleeve threadedly engages a proximal end of the second sleeve.

* * * * *